US010882821B1

(12) United States Patent
Cohen et al.

(10) Patent No.: US 10,882,821 B1
(45) Date of Patent: Jan. 5, 2021

(54) ENANTIOMERIC COMPOUND FOR THE REDUCTION OF THE DELETERIOUS ACTIVITY OF EXTENDED NUCLEOTIDE REPEAT CONTAINING GENES

(71) Applicant: THE BOARD OF TRUSTEES OF THE LELAND STANFORD JUNIOR UNIVERSITY, Stanford, CA (US)

(72) Inventors: Stanley N. Cohen, Stanford, CA (US); Ning Deng, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 8 days.

(21) Appl. No.: 16/137,395

(22) Filed: Sep. 20, 2018

Related U.S. Application Data

(60) Provisional application No. 62/563,522, filed on Sep. 26, 2017, provisional application No. 62/618,001, filed on Jan. 16, 2018.

(51) Int. Cl.
*C07D 209/70* (2006.01)
*A61P 25/28* (2006.01)

(52) U.S. Cl.
CPC ............ *C07D 209/70* (2013.01); *A61P 25/28* (2018.01)

(58) Field of Classification Search
CPC ................................ C07D 209/70; A61P 25/28
See application file for complete search history.

(56) References Cited

U.S. PATENT DOCUMENTS

| | | | |
|---|---|---|---|
| 5,100,891 A | 3/1992 | Ong et al. |
| 5,514,700 A | 5/1996 | Ong et al. |
| 5,827,871 A | 10/1998 | King et al. |
| 6,620,840 B1 | 9/2003 | Bigg et al. |
| 6,747,024 B1 | 6/2004 | Auvin et al. |
| 7,419,997 B2 | 9/2008 | Boggs et al. |
| 7,622,494 B2 | 11/2009 | Boggs et al. |
| 8,003,692 B2 | 8/2011 | Schein et al. |
| 8,808,880 B2 | 8/2014 | Kim et al. |
| 8,946,444 B2 | 2/2015 | Lennox et al. |
| 9,271,960 B2 | 3/2016 | Lennox et al. |
| 2007/0276009 A1 | 11/2007 | Ni et al. |
| 2009/0170906 A1 | 7/2009 | Gudmundsson et al. |
| 2009/0170923 A1 | 7/2009 | Gudmundsson |
| 2010/0210661 A1 | 8/2010 | Sekiguchi et al. |
| 2011/0218241 A1 | 9/2011 | Preston et al. |
| 2015/0210717 A1 | 7/2015 | Gines et al. |

FOREIGN PATENT DOCUMENTS

| | | |
|---|---|---|
| WO | WO2004110999 A1 | 12/2004 |
| WO | WO2005023245 A1 | 3/2005 |
| WO | WO2009077068 A1 | 6/2009 |
| WO | WO2010010027 A1 | 1/2010 |
| WO | WO2013139929 A1 | 9/2013 |
| WO | WO2016008010 A1 | 1/2016 |
| WO | WO2016116603 A1 | 7/2016 |
| WO | WO2016196012 A1 | 12/2016 |
| WO | WO2018236910 A1 | 12/2018 |

OTHER PUBLICATIONS

Gudmundsson et al., Bioorganic & Medicinal Chemistry Letters 19 (2009) 3489-3492.*
Czeredys et al. "Tetrahydrocarbazoles decrease elevated SOCE in medium spiny neurons from transgenic YAC128 mice, a model of Huntington's disease," Biochemical and Biophysical Research Communications 483 (2017) 1194-1205.
Gudmundsson et al. "Substituted tetrahydrocarbazoles with potent activity against human papillomaviruses," Bioorg. Med. Chem. Lett., 19(13), 3489-3492 (2009). Abstract Only.
Honarnejad et al. "Identification of tetrahydrocarbazoles as novel multifactorial drug candidates for treatment of Alzheimer's disease," Translational Psychiatry (2014), 4(12), e489.
Süssmuth et al. "An exploratory double-blind, randomized clinical trial with selisistat, a SirT1 inhibitor, in patients with Huntington's disease," Br. J. Clin. Pharmacol., 79:3, 465-476 (2014).

* cited by examiner

*Primary Examiner* — Alicia L Otton
(74) *Attorney, Agent, or Firm* — Bret E. Field; Bozicevic, Field & Francis LLP

(57) ABSTRACT

Aspects of the present disclosure include methods of reducing the deleterious impact of a target gene in a cell, such as the deleterious activity of a mutant extended nucleotide repeat (NR) containing target gene in a cell, by contacting the cell with an effective amount of an enantiomeric tetrahydrocarbazolamine compound. The deleterious activity (e.g., toxicity and/or dis-functionality of products encoded thereby) of a mutant extended NR containing target gene may be reduced, e.g., by reducing (and in some instances differentially, including selectively, reducing) the production or activity of toxic expression products (e.g., RNA or protein) encoded by the target gene. Kits and compositions for practicing the subject methods are also provided.

20 Claims, 5 Drawing Sheets

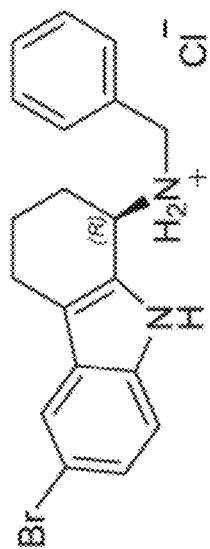
FIG. 5C
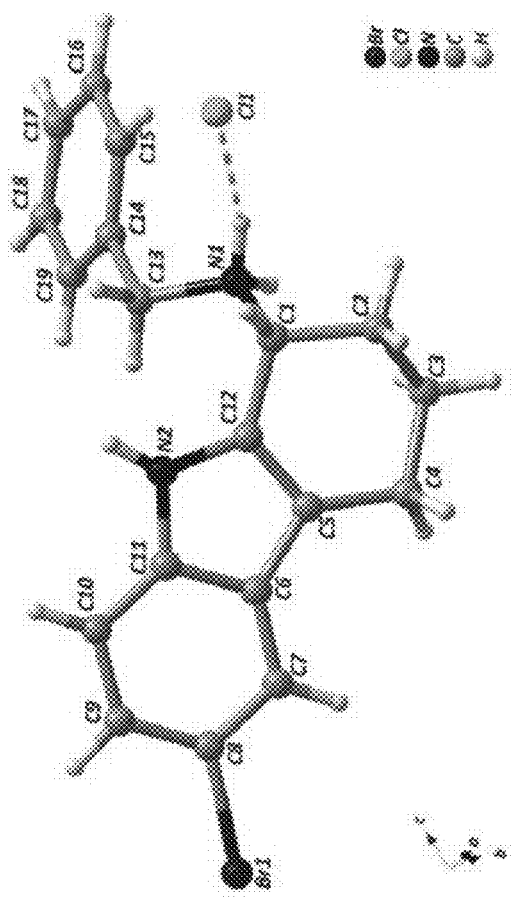
FIG. 5A
FIG. 5B

ENANTIOMERIC COMPOUND FOR THE REDUCTION OF THE DELETERIOUS ACTIVITY OF EXTENDED NUCLEOTIDE REPEAT CONTAINING GENES

CROSS-REFERENCE TO RELATED APPLICATIONS

This application claims priority to U.S. Provisional Application Ser. No. 62/618,001, filed Jan. 16, 2018, and U.S. Provisional Application Ser. No. 62/563,522, filed Sep. 26, 2017; the disclosures of which applications are herein incorporated by reference.

This invention was made with Government support under contract TR001085 awarded by the National Institutes of Health, and under contract NS085812 awarded by the National Institutes of Neurological Disorders and Stroke. The Government has certain rights in the invention.

INTRODUCTION

Abnormal expansion of nucleotide repeats in coding or non-coding DNA regions have been associated with many disease conditions. These mutant regions of expanded repeats may result in mutant gene products that cause disease through a variety of different mechanisms, e.g., loss- or gain-of-function mechanisms, e.g., as a result of toxic RNA, altered RNA processing, misfolded and abnormal proteins, reduced gene expression and altered protein function.

Long repeats may form unusual DNA structures that can increase the likelihood of expansion or sometimes contraction. Models explaining the dynamic behavior of repeat regions also involve slipped strand mispairing during DNA replication or repair, misalignment and excision repair, and unequal crossing-over. Due to somatic and germline instability of the repeat regions, families with repeat mutations may see an increase in disease severity and an earlier age of onset from one generation to the next, a phenomenon known as anticipation.

Certain trinucleotide repeat diseases result from repeats occurring in non-coding sequences, and such repeats may result in loss of function of the affected gene. Trinucleotide repeat sequences implicated in diseases include CGG, GCC, GAA, CTG, and CAG units. The nature of the sequence itself and the location of repeats can affect the mechanism of disease pathogenesis. X-linked trinucleotide diseases are Fragile X syndrome (FRAXA), Fragile XE MR (FRAXE) and Fragile X tremor/ataxia syndrome (FXTAS). This group of diseases includes both loss of function mutations and the production of toxic RNA. Autosomal diseases include myotonic dystrophy, Friedreich's ataxia and two types of spinocerebellar ataxia (SCA8 and SCA12). Phenotypic manifestations of a disease are highly variable, and pathogenic mechanisms also vary from disease to disease.

Polyglutamine repeat diseases are a particular trinucleotide repeat disease category. These diseases result from exonic repeats that are located in protein-coding regions of genes and code for polyglutamine tracts in the proteins encoded by these genes. Subsets of neurons are especially vulnerable to polyglutamine repeat disease mechanisms. The following examples are known polyglutamine repeat diseases: Dentatorubral-pallidoluysian atrophy (DRPLA), Huntington's disease, spinobulbar muscular dystrophy, and spinocerebellar ataxia types 1, 2, 3, 6, 7, and 17. Hunting-ton's Disease-like 2 can result from pathogenic polyglutamine repeat mechanisms. Polyglutamine repeat diseases commonly produce symptoms that have an onset relatively late in life and lead to progressive neuronal dysfunction and ultimately, to severe neurodegeneration. A hallmark of these diseases is the presence of aggregates of proteins containing polyglutamine tracts, mainly found in the nucleus of affected neurons. Misfolded repeat containing proteins may be toxic, and protein aggregates may have altered interactions with transcriptional regulators. However, the exact pathogenic mechanism is complex. Not only do repeat expansions affect genes encoding proteins with dissimilar functions, but polyglutamine repeat diseases can also manifest in different regions of the brain. Polyglutamine repeat proteins may play a role in inappropriately activating a cell's apoptotic pathway, leading to cell death.

Nucleotide repeats encoding polyalanine tracts have also been found to cause disease. For example trinucleotide repeats encoding alanine tracts have been linked to congenital malformation syndromes. Affected genes encode transcription factors that play roles during development, and the repeats lead to misfolded proteins and protein aggregation and degradation. Unstable regions of various other sizes of nucleotide repeat units are also the basis for disease. Tetranucleotide repeats cause myotonic dystrophy type 2, and pentanucleotide repeats result in SCA 10 and SCA 31. Dodecamer repeats have been implicated in progressive myoclonic epilepsy.

Expansion of trinucleotide repeats in gene segments that do not encode proteins can cause disease by producing abnormal RNAs. Furthermore, repeat expansions need not necessarily involve trinucleotides. For example, expansion of the GGGGCC hexanucleotide repeat in non-coding regions of C9ORF72 is the most common cause of two diseases, autosomal-dominant frontotemporal dementia (FTD) and amyotrophic lateral sclerosis (ALS). Individuals afflicted with this autosomal dominant mutation experience deficits in executive function and behavioral changes (FTD) or motor neuron dysfunction (ALS). Some patients may have a combination of FTD and ALS symptoms. C9ORF72 hexanucleotide repeats are also rarely associated with parkinsonism, pseudodementia, psychiatric disorders, and other neurological diseases. While the number of hexanucleotide repeats in C9ORF72 normally is fewer than 25, mutant repeat regions can contain up to 1500 or more hexanucleotide units. Studies propose that the hexanucleotide repeat regions are unstable and that abnormally long repeats may occur on a predisposing haplotypic background prone to expansion.

SUMMARY

Aspects of the present disclosure include methods of reducing the deleterious impact of a target gene in a cell, such as the deleterious activity of a mutant extended nucleotide repeat (NR) containing target gene in a cell, by contacting the cell with an effective amount of an enantiomeric tetrahydrocarbazolamine compound. The deleterious activity (e.g., toxicity and/or dis-functionality of products encoded thereby) of a mutant extended NR containing target gene may be reduced, e.g., by reducing (and in some instances differentially, including selectively, reducing) the production or activity of toxic expression products (e.g., RNA or protein) encoded by the target gene. Kits and compositions for practicing the subject methods are also provided.

BRIEF DESCRIPTION OF THE DRAWINGS

FIG. 5A to FIG. 5C illustrates the chirality determination of (+)-HD143 by X-ray crystallography. FIG. 5A shows a depiction of the asymmetric unit of (R)-(+)-HD143 hydrochloride single crystal. FIG. 5B shows a thermal ellipsoids drawing of (R)-(+)-HD143 cation and chloride ion in the crystal lattice. FIG. 5C depicts the structure of (R)-(+)-HD143.

DEFINITIONS

Figure 1:
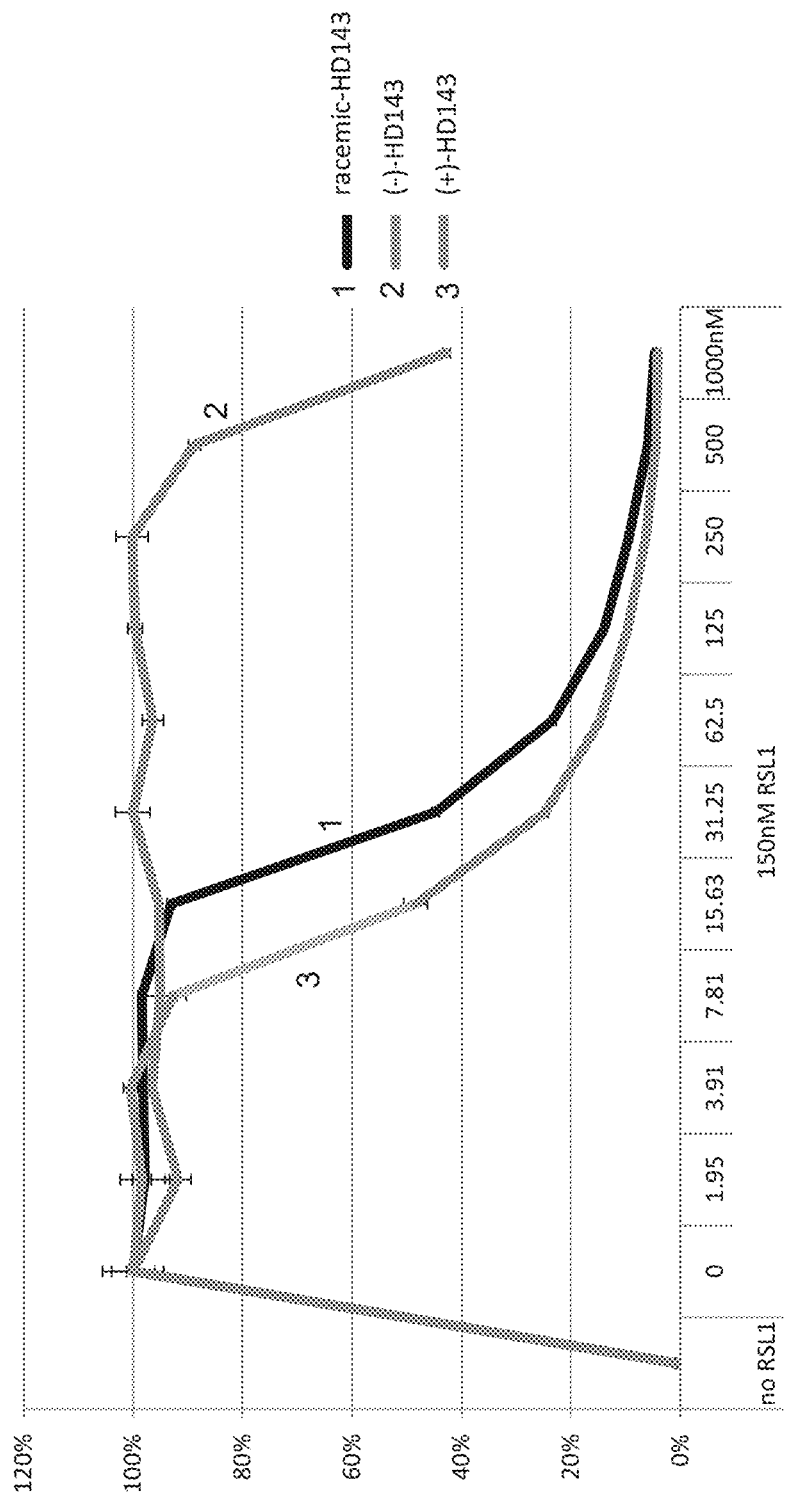
FIG. 1 shows a graph of activity data for racemic-HD143 versus the (R)-(+)-HD143 and (S)-(−)-HD143 enantiomers as tested in a split *Gaussia* luciferase complementation assay, as reported in the Experimental Section, below. (R)-(+)-HD143 is 2 fold more potent than racemic HD143 ($IC_{50}$=15 nM vs. $IC_{50}$=30 nM), while (S)-(–)-HD143 is much less active ($IC_{50}$=900 nM). This result indicates that (R)-(+)-HD143 is the active component of racemic HD143.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein, unless stated otherwise. Enantiomeric and stereoisomeric mixtures can be resolved into their component enantiomers or stereoisomers using separation techniques or chiral synthesis techniques. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature.

Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Enantiomer" refers to one of a pair of chiral molecules that are mirror images of each other. Enantiomers can be referred to as (+) or (–) enantiomers. Enantiomers can be referred to as (S)- or (R)-enantiomers.

The term "racemic" or "racemate", and other like terms refer to generally equimolar proportions of a (+)-enantiomer and a (–)-enantiomer of a compound in a composition.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

Other definitions of terms may appear throughout the specification.

DETAILED DESCRIPTION

As summarized above, aspects of the present disclosure include methods of reducing the deleterious impact of a target gene in a cell, such as the deleterious activity of a mutant extended nucleotide repeat (NR) containing target gene in a cell, by contacting the cell with an effective amount of an enantiomeric tetrahydrocarbazolamine compound. The deleterious activity (e.g., toxicity and/or dis-functionality of products encoded thereby) of a mutant extended NR containing target gene may be reduced, e.g., by reducing (and in some instances differentially, including selectively, reducing) the production or activity of toxic expression products (e.g., RNA or protein) encoded by the target gene. Kits and compositions for practicing the subject methods are also provided. Methods, kits and compositions of the invention find use in a variety of different applications, including the prevention or treatment of disease conditions associated with the presence of genes containing mutant extended nucleotide repeats, e.g., mutant extended trinucleotide repeats, such as Huntington's Disease (HD).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Enantiomeric Compound

Aspects of the present disclosure include an enantiomeric tetrahydrocarbazolamine compound and compositions including the same which find use in reduction of the deleterious impact in a cell of a target gene that includes an extended nucleotide repeat (NR). In some instances, the enantiomeric compound is of the following formula (I):

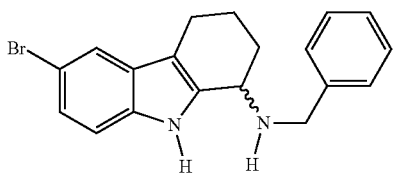

(I)

wherein the compound is the (R)-(+)-enantiomer, or a salt thereof. The enantiomeric compound can also be referred to as (R)-(+)-N-benzyl-6-bromo-2,3,4,9-tetrahydro-1H-carbazol-1-amine or (R)-(+)-HD143. Where a compound is described as a single enantiomer, it is understood that a sample of the compound may still contain some amounts of the opposite enantiomer. The subject compound and compositions of the present disclosure can be enriched in the (R)-(+)-enantiomer that displays significant in vitro and/or in vivo activity. By the term "enriched" is meant when the weight:weight ratio of the enantiomers is at least approximately 1.05 or higher in favor of the enantiomer that displays significant in vitro and in vivo activity (the (R)-(+)-enantiomer).

In some instances, the subject compound and compositions of the present disclosure are substantially enriched in the (R)-(+)-enantiomer that displays significant in vitro and/or in vivo activity. By the term "substantially enriched" is meant the weight:weight ratio of the enantiomers is about 1.5 or higher in favor of the (R)-(+) enantiomer over the (S)-(−)-enantiomer. In certain embodiments, the composition is substantially enriched in the (R)-(+)-enantiomer by a weight:weight ratio that is about 2 or greater, about 3 or greater, about 4 or greater, such as about 5 or greater, about 6 or greater, about 7 or greater, about 8 or greater, about 9 or greater, about 10 or greater, or about 20 or greater in favor of the (R)-(+)-enantiomer that displays significant in vitro and/or in vivo activity over the (S)-(−)-enantiomer.

The term "enantiomerically enriched" or "enriched enantiomer" denotes that the compound comprises 75% or more by weight of the enantiomer, such as 80% or more by weight, 85% or more by weight, more than 90% or more by weight, more than 91% or more by weight, more than 92% or more by weight, more than 93% or more by weight, more than 94% or more by weight, more than 95% or more by weight, more than 96% or more by weight, or more than 97% or more by weight of the enantiomer.

The term "enantiomerically enriched (R)-(+)-N-benzyl-6-bromo-2,3,4,9-tetrahydro-1H-carbazol-1-amine" refers to the compound comprising 75% or more by weight (R)-(+)-enantiomer and at most 25% by weight (S)-(−)-enantiomer, such as 80% or more by weight (R)-(+)-enantiomer and at most 20% by weight (S)-(−)-enantiomer, 90% or more by weight (R)-(+)-enantiomer and at most 10% by weight (S)-(−)-enantiomer, 91% or more by weight (R)-(+)-enantiomer and at most 9% by weight (S)-(−)-enantiomer, 92% or more by weight (R)-(+)-enantiomer and at most 8% by weight (S)-(−)-enantiomer, 93% or more by weight (R)-(+)-enantiomer and at most 7% by weight (S)-(−)-enantiomer, 94% or more by weight (R)-(+)-enantiomer and at most 6% by weight (S)-(−)-enantiomer, 95% or more by weight (R)-(+)-enantiomer and at most 5% by weight (S)-(−)-enantiomer, 96% or more by weight (R)-(+)-enantiomer and at most 4% by weight (S)-(−)-enantiomer, or 97% or more by weight (R)-(+)-enantiomer and at most 3% by weight (S)-(−)-enantiomer.

In certain embodiments, the enantiomeric tetrahydrocarbazolamine compound is enantiomerically pure (R)-(+)-N-benzyl-6-bromo-2,3,4,9-tetrahydro-1H-carbazol-1-amine.

The term "enantiomerically pure" refers to a compound that is present in enantiomeric excess of greater than 95%. In some cases, the enantiomeric excess is greater than 96%. In some cases, the enantiomeric excess is greater than 97%. In some cases, the enantiomeric excess is greater than 98%. In certain instances, the enantiomeric excess is greater than 99%. The term "enantiomeric excess" refers to a difference between the amount of one enantiomer (e.g., (R)-(+)-enantiomer) and the amount of the other enantiomer (e.g., (S)-(−)-enantiomer) that is present in a compound composition. Thus for example, enantiomeric excess of 96% refers to a compound composition having 98% of one enantiomer and 2% of the other enantiomer.

Aspects of the present disclosure include an enantiomeric tetrahydrocarbazolamine compound (e.g., as described herein), salts thereof (e.g., pharmaceutically acceptable salts), and/or solvate, hydrate and/or prodrug forms thereof. It will be appreciated that all permutations of salts, solvates, hydrates, and prodrugs are meant to be encompassed by the present disclosure.

In some embodiments, the enantiomeric tetrahydrocarbazolamine compound, or a prodrug form thereof, are provided in the form of a pharmaceutically acceptable salt.

Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject enantiomeric tetrahydrocarbazolamine compound is provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject enantiomeric tetrahydrocarbazolamine compound, prodrugs, or salts thereof is provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include an enantiomeric tetrahydrocarbazolamine compound (e.g., as described herein) (either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which an enantiomeric tetrahydrocarbazolamine compound is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compound and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient is determined in part by the compound, as well as by the particular method used to administer the composition. Accordingly, there is a wide variety of suitable formulations of the subject pharmaceutical compositions.

Administration of the subject compound may be systemic or local. In certain embodiments administration to a mammal will result in systemic release of the compound (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compound and compositions of the present disclosure are administered subcutaneously. In certain embodiments, the compound and compositions of the present disclosure are administered orally. In certain embodiments, it may be desirable to administer the enantiomeric tetrahydrocarbazolamine compound locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The enantiomeric tetrahydrocarbazolamine compound can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The enantiomeric tetrahydrocarbazolamine compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments, the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the subject compound or composition. Similarly, unit dosage forms for injection or intravenous administration may include the enantiomeric tetrahydrocarbazolamine compound in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the enantiomeric tetrahydrocarbazolamine compound calculated in an amount sufficient to produce the desired effect in association with a pharmaceutically acceptable diluent, carrier or vehicle. The specifications for the novel unit dosage forms of the present disclosure depend on the compound and the effect to be achieved, and the pharmacodynamics associated with the compound in the host. In pharmaceutical dosage forms, the enantiomeric tetrahydrocarbazolamine compound may be administered in the form of a free base, a pharmaceutically acceptable salt, or the compound may also be used alone or in appropriate association, as well as in combination, with other pharmaceutically active compounds.

Dose levels can vary as a function of the specific composition, the nature of the delivery vehicle, and the like. Desired dosages for the enantiomeric tetrahydrocarbazolamine compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the compound employed, the condition of the animal, and the body weight of the animal, as well as the severity of the illness and the stage of the disease. The size of the dose will also be determined by the existence, nature, and extent of any adverse side-effects that might accompany the administration of the enantiomeric tetrahydrocarbazolamine compound.

Methods

Aspects of the present disclosure include methods for reducing the deleterious impact in a cell of a target gene that includes an extended nucleotide repeat (NR) by contacting the cell with an effective amount of the enantiomeric tetrahydrocarbazolamine compound (e.g., as described herein). Further aspects of the methods in which the subject compound finds use are described by Cohen et al. in WO 2016/196012, the disclosure of which is herein incorporated by reference in its entirety. Embodiments of the present disclosure include methods of reducing an extended nucleotide repeat-containing target gene's deleterious (e.g., harmful or injurious) activity in a cell. As used herein, the term "deleterious impact" refers to a harmful or injurious activity associated with, or attributable to, a target gene and any undesirable effect on the cell which may result from such activity. As used herein, the term "deleterious activity" refers to a harmful or injurious activity associated with, or attributable to, a target gene. By "reducing deleterious impact" or "reducing deleterious activity" is meant that the level of a harmful or injurious activity, or an undesirable effect thereof, is reduced by a statistically significant amount, and in some instances by 2-fold or more, such as by 5-fold or more, by 10-fold or more, by 20-fold or more, by 50-fold or more, by 100-fold or more, or even more, as compared to a control, e.g., a cell not contacted with the subject compound. The deleterious impact or activity of the target gene that is reduced by the subject compounds may vary, and may include, but is not limited to, cell toxicity, reduction in cell viability, loss of cellular function, formation of protein aggregates, etc. The subject methods, compound and compositions may reduce the deleterious impact or activity of the target gene in a cell, via a method as described by Cheng, Cohen et al. "Selective reduction of the deleterious activity of extended tri-nucleotide repeat containing genes" WO 2012078906, and Cohen et al. WO 2016196012, the disclosures of which is herein incorporated by reference in its entirety.

In certain embodiments, the methods may reduce the deleterious impact of an extended NR containing target gene by differentially reducing the deleterious impact of the target gene. In some embodiments, the subject compound modulates expression of the RNA and/or protein from the gene, such that it changes the expression of the RNA or protein from the target gene in some manner. In certain embodiments of the method, the subject compound modulates expression of the protein from the target gene. In certain cases of the method, the subject compound differentially, and in some instances selectively, reduces transcription of the target gene to reduce toxicity in the cell of a protein encoded by the target gene. Any convenient assays may be used to determine a reduction in transcription in a cell using the subject compound relative to a control, e.g., a cell not contacted with the compound, where the magnitude of transcription reduction may be 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more. In some instances of the method, the subject compound differentially, and in some instances selectively, reduces transcription of the target gene to enhance functionality of the protein in the cell. By enhance functionality is meant that a natural, desirable function or activity of a protein encoded by the target gene is increased relative to a control, e.g., a cell not contacted with the compound, by 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more. Any convenient assays may be utilized to determine the level of function or activity of a protein of interest. By differentially reducing transcription of the target gene is meant that transcription of the target gene is reduced to an extent that is greater than any reduction of the non-target, e.g., corresponding wild-type, gene. The magnitude of any difference in transcription resulting from administration of the compound may vary, where in some instances the magnitude of reduction of target gene transcription relative to corresponding non-target gene transcription is 2-fold or more, by 5-fold or more, by 10-fold or more, by 20-fold or more, by 50-fold or more, by 100-fold or more, or even more. In some instances, while transcription of the target gene is reduced, administration of the compound results in substantially little, if any, transcription reduction of the corresponding non-target gene. In such instances, administration of the compound may be viewed as selectively reducing transcription of the target gene.

In certain embodiments, the methods may reduce the deleterious impact of an extended NR containing target gene by selectively reducing the deleterious impact of the target gene. As the methods of these embodiments are methods of selectively reducing the deleterious impact, i.e., activity, of the target gene, they do so while retaining at least a statistically measurable amount of normal or wild-type, e.g., beneficial, activity of the target gene, by which is meant the activity of the gene as present in normal or wild-type cells, which are cells in which the target gene does not include mutant extended nucleotide repeats (e.g., trinucleotide repeats) that give rise to deleterious activity. Accordingly, in these embodiments the subject methods may maintain or restore a physiologically desirable activity of the target gene despite the selective reduction of the harmful activity of the target gene. In some instances of the method, the compound modulates the activity of a protein encoded by the target gene. In some embodiments of the method, the expression of the protein from the target gene is selectively modulated relative to expression from a normal allele of the target gene (e.g., a normal allele of the target gene includes 8 to 25 CAG repeats). In certain cases, the activity of a normal allele of the target gene is maintained in the cell, e.g., has an activity that is within 20% (such as within 10%, within 5%, within 2% or within 1%) of the corresponding activity of a control cell not contacted with the compound of interest.

In yet other embodiments, the methods may reduce the deleterious impact in a cell of an extended NR containing target gene by reducing the deleterious impact as well as any normal activity of the target gene. As the methods of these embodiments are methods of non-selectively reducing the deleterious impact, i.e., activity, of the target gene, they reduce the deleterious impact of the target gene while also reducing to some extent, if not completely, the normal or wild-type, e.g., beneficial, activity of the target gene, by which is meant the activity of the gene as present in normal or wild-type cells, which are cells in which the target gene does not include mutant extended nucleotide repeats (e.g., TNRs) that give rise to deleterious activity.

In some cases, the harmful or injurious activity is a dysfunction of a protein product encoded by the target gene, where the dysfunction refers to an undesirable activity (e.g., cell toxicity) of the protein product that is not present in a normal allele of the target gene. In some instances, a target gene that does not include mutant extended nucleotide repeats that give rise to deleterious activity is referred to as a normal allele of the target gene. The normal allele of the target gene may include a desirable number of nucleotide repeats (NRs). In certain instances where the NR is a TNR, the normal allele includes 25 or less tri-nucleotide repeats (TNRs), such as 20 or less or 10 or less TNRs. In certain cases, the normal allele of the target gene includes 8 to 25 TNRs. In some instances, the normal allele includes 8 to 25 CAG repeats.

In certain embodiments of the method, the deleterious impact of the target gene is toxicity of the protein and the compound reduces the toxicity of the protein in the cell. In some instances, toxicity is a result of undesirable protein aggregation. As such, in some instances the subject methods result in a reduction in toxicity that is attributable to the target gene, where the magnitude of the toxicity reduction may vary, and in some instances is 2-fold or greater, such as by 5-fold or greater, by 10-fold or greater, by 20-fold or greater, by 50-fold or greater, by 100-fold or greater, or even greater. e.g., as compared to a suitable control, e.g., a cell not contacted with the compound. As described in greater detail below, toxicity may be reduced in a number of different ways that may depend on the particular target gene. In some instances, e.g., where the target gene includes an extended CAG repeat that results in the presence of extended polyQ domains in a product encoded by the target gene, toxicity reduction may be accompanied by a reduction in aggregation of the products encoded by the target gene. In some embodiments of the method, the protein forms aggregates in the cell and includes a polyglutamine stretch with 26 or more glutamine residues, such as 30 or more glutamine residues, 35 or more, 40 or more, 50 or more, or 60 or more glutamine residues.

In such instances, the magnitude of the reduction in aggregation may vary, and in some instances the magnitude of reduction is 2-fold or more, such as by 5-fold or more, by 10-fold or more, by 20-fold or more, by 50-fold or more, by 100-fold or more, or even more, e.g., as compared to a suitable control, e.g., a cell not contacted with the compound of interest. Protein aggregation may be assayed using any convenient protocol, including but not limited to, the protocols described in Published United States Patent Application No. 20110130305; the disclosure of which protocols are herein incorporated by reference.

In certain embodiments, the deleterious impact or activity that is reduced by methods of the invention may be loss of function of a product encoded by the target gene. In certain of these embodiments, the wild-type or normal activity of the product encoded by the target gene is at least partially, if not completely, impaired because the target gene includes the extended trinucleotide repeat. In these instances, the loss of function is at least partially, if not completely, reversed by enhancing the desired function of the product of the target gene. The desired function of the encoded product may be enhanced by a statistically significant amount as compared to a suitable control, e.g., a cell not contacted with the compound of interest, where the magnitude of the enhancement in desired activity may be 2-fold or higher, such as 5-fold or higher, including 10-fold or higher.

In certain embodiments, the subject compound increases the viability of the cell, as compared to a suitable control and as determined by a cell viability assay, e.g., as determined by contacting the cell with a compound of the present disclosure to a cell and determining the number of viable cells in culture using a homogeneous method, such as the CellTiter-Glo® Luminescent Cell Viability Assay.

The target gene is a gene that includes a mutant extended NR, such as a TNR, where the mutant extended nucleotide repeat domain is not present in normal versions of the gene. The term "gene" as used herein is a defined region or portion of a chromosome that encodes or enables production of a product and includes a promoter, introns, exons and enhancers. By mutant extended nucleotide repeat (NR) is meant a domain (i.e., region) of the gene that includes multiple adjacent repeats of units of 2 or more nucleotides, where a given repeating unit of nucleotides may vary in length, ranging in some instances from 2 to 10 nucleotides, such as 3 to 6 nucleotides, where examples of repeat unit lengths include units of 2 nucleotides (e.g., where the mutant extended nucleotide repeat is a dinucleotide repeat), 3 nucleotides (e.g., where the mutant extended nucleotide repeat is a trinucleotide repeat), 4 nucleotides (e.g., where the mutant extended nucleotide repeat is a tetranucleotide repeat), 5 nucleotides (e.g., where the mutant extended nucleotide repeat is a pentanucleotide repeat) or 6 nucleotides (e.g., where the mutant extended nucleotide repeat is a hexanucleotide repeat). Within a given domain, the domain may be homogeneous or heterogeneous with respect to the nature of the repeat units that make up the domain. For example, a given domain may be made up of a single type of repeat unit, i.e., al the repeat units of the domain share the same (i.e., identical) sequence of nucleotides, such that it is a homogeneous mutant NR domain. Alternatively, a given domain may be made up of two or more different types of repeat units, i.e., repeat units that have differing sequences, such that it is a heterogeneous mutant NR domain. The mutant extended nucleotide repeat domain may be present in a coding or non-coding region of the target gene. In some instances, the extended nucleotide repeat domain is present in a coding region of the target gene. In some instances, the extended nucleotide repeat domain is present in a non-coding region of the target gene. The length and particular sequence of the mutant extended nucleotide repeat may vary.

In some instances, the mutant extended nucleotide repeat is a mutant extended trinucleotide repeat. By mutant extended trinucleotide repeat is meant a domain (i.e., region) of the gene that includes multiple adjacent repeats of the same three nucleotides, where the length and particular sequence of the mutant extended trinucleotide repeat may vary and the mutant extended trinucleotide repeat domain is not present in normal versions of the gene. The extended trinucleotide repeat domain may be present in a coding or non-coding region of the target gene. In some instances, the extended trinucleotide repeat domain is present in a coding region of the target gene. In some instances, the extended trinucleotide repeat domain is present in a non-coding region of the target gene. In embodiments, the mutant repeat domain is present in a non-coding region of the target gene, such as the CTG expansion located in the 3' untranslated region of the dystrophia myotonica-protein kinase gene, which leads to Myotonic dystrophy (DM). In some instances, the mutant repeat domain is present in a coding region of the target gene, such that in some instances its presence in the target gene results in a corresponding domain or region (e.g., polyQ domain) in a product encoded by the gene. In some instances of the method, the mutant extended TNR domain is a CTG repeat domain. In certain cases, the mutant extended trinucleotide repeat domain includes 26 or more CTG repeats (e.g., 30 or more, 35 or more, etc.).

The mutant extended trinucleotide repeat may vary in terms of nucleotide composition and length. Specific trinucleotides of interest include, but are not limited to: CAG, CTG, CGG, GCC, GAA, and the like. In some instances, the mutant extended trinucleotide repeat domain is a CAG repeat domain. The particular length of the repeat domain (e.g., CAG repeat domain) may vary with the respect to the specific target gene so long as it results in deleterious activity, and in some instances is 25 repeats or longer, such as 26 repeats or longer, 30 repeats or longer, including 35 repeats or longer, 40 repeats or longer, 50 repeats or longer or even 60 repeats or longer. Specific target genes and expressed proteins of interest, diseases associated therewith and the specific length of repeat sequences of extended CAG repeats of interest, include (but are not limited to) those provided in Table 1, below.

TABLE 1

| Disease | disease name/protein product | | Pathogenic repeat length |
|---|---|---|---|
| Spinocerebellar ataxia type 1 | SCA1 | SCA1/ataxin 1 | 40~82 |
| Spinocerebellar ataxia type 2 | SCA2 | SCA2/ataxin 2 | 32~200 |
| Spinocerebellar ataxia type 3 | SCA3(MJD) | SCA3/ataxin 3 | 61~84 |
| Spinocerebellar ataxia type 7 | SCA7 | SCA7/ataxin 7 | 37~306 |
| Spinocerebellar ataxia type 17 | SCA17 | SCA17/TBP | 47~63 |
| Dentatorubral pallidoluysian atrophy | DRPLA | DRPLA/atrophin 1 | 49~88 |
| Spinal and bular muscular atrophy | SBMA | Kennedy's disease/androgen receptor protein | 38~62 |
| Huntington's disease | HD | Huntington's Disease/huntingtin protein | 40~121 |

The pathogenic repeat lengths shown are approximate and represent the most common range of pathogenic repeat lengths. The lower of the two numbers shown for each pathogenic repeat length indicates the length at which pathogenic effects of the expansion begin to occur. Although both cellular copies of autosomal genes responsible for NR diseases may contain NR domains, commonly one copy of the targeted gene is mutated to have an expanded NR segment, whereas the other copy (i.e., allele) contains a unexpanded NR.

As summarized above, the deleterious activity (e.g., toxicity and/or dis-functionality of products encoded thereby) of a mutant extended NR containing target gene may be reduced by the subject compound in a variety of different ways, e.g., by reducing (and in some instances selectively reducing) the production or activity of toxic expression products (e.g., RNA or protein) encoded by the target gene, as described in greater detail below.

In some embodiments of the method, the subject compound modulates the activity of a protein encoded by the target gene. For example, with respect to polyQ repeats, in certain embodiments, the target gene is selected from genes that produce the following diseases: SCA1, SCA2, SCA3, SCA7, SCA17, DRPLA, Kennnedy's Disease, amyotrophic lateral sclerosis (ALS) and Huntington's Disease. In certain instances, the targeted disease is SCA1. In certain instances, the target disease is SCA2. In certain instances, the target disease is SCA3. In certain instances, the target disease is SCA7. In certain instances, the target disease is SCA17. In certain instances, the target disease is DRPLA. In certain instances, the target disease is Kennedy's Disease. In certain cases, the target disease is amyotrophic lateral sclerosis (ALS). In certain instances, the target disease is Huntington's Disease. Genes and their encoded proteins that give rise to these diseases are listed in Table 1, above. Any protein that is encoded by the target gene may be modulated, include post-translationally modified proteins. The modulated protein may be any expressed product of the gene, or a post-transcriptionally modified version thereof. In some cases, the protein is a Htt protein. In certain cases, the protein is a mutant Htt protein. Any post-translational modifications of huntingtin (Htt) proteins of interest may be modulated. Post-translational modifications of proteins of interest may regulate protein stability, localization, function, and their interactions with other molecules. Post-translational modifications may occur as chemical modifications at amino acid residues, including SUMOylation, phosphorylation, palmitoylation, acetylation, etc. Post-translational modifications may include enzymatic cleavage. Post-translational modifications may be involved in the regulation and control of a variety of cellular processes, such as Htt metabolism, protein-protein interactions and cellular toxicity.

In some instances, the subject compound modulates the functionality, e.g., binding properties, activity, etc., of the protein following expression, such that the compound is one that changes the functionality of the protein encoded by the target gene following expression of the protein from the target gene. In some cases, the compound may be one that differentially reduces the deleterious functionality, e.g., aggregation, of the encoded protein, but retains or enhances, at least to a detectable level, the beneficial activity of the encoded protein. In some cases, the compound may be one that selectively reduces the deleterious functionality, e.g., aggregation, of the encoded protein, but retains or enhances, at least to a detectable level, the beneficial activity of the encoded protein. In certain embodiments, the subject compound isnot an inhibitor of aggregation of the protein, but instead selectively reduce the deleterious activity or functionality of the protein via another mechanism, e.g., by reducing the amount of the protein in the cell that is available for aggregation, by reducing production of a protein that is detrimental to cells independently of its propensity to aggregate, etc.

In some cases, the subject compound may change expression of a gene product, e.g., an RNA or protein. In certain embodiments of the method, the subject compound reduces the deleterious impact by modulating functionality, e.g., changing binding interactions, of a SPT4 protein in the cell. The term SPT4 protein is used herein to collectively refer to not only yeast Spt4 proteins, but also mammalian homologs thereof, e.g., human SUPT4H; murine Supt4h, etc. As such, SPT4 proteins of interest whose activity may be modulated by the selective a SPT4 modulatory compound include, but are not limited to: S. cerevisiae Spt4; human SUPT4H and murine Supt4h. The subject compoundmay be referred to as a SPT4 modulatory agent. SPT4 modulatory agents are compounds that change the SPT4 activity in a cell, e.g., decrease SPT4 activity in a cell. The compound may be a selective SPT4 modulatory agent. In some instances, the target SPT4 activity that is modulated, e.g., decreased, by the active compound is a transcription activity, and specifically an activity that facilitates RNA polymerase II processivity through long trinucleotide repeat domains, e.g., long CAG repeat domains. The target SPT4 activity that is modulated by a subject compound can be an activity arising from an SPT4 protein.

Where the subject compound employed in methods of the invention is an SPT4 modulatory agent, the compound may, upon introduction into a cell, change the SPT4 functionality in the cell, and at least differentially reduce the extended trinucleotide repeat mediated SPT4 transcription activity in the subject. The SPT4 modulatory agent may modulate functionality in a variety of ways, e.g., by inhibiting binding of an SPT4 protein to another protein, e.g., a protein interacting with SPT4 (e.g., an SPT5 protein, such as Spt5 or SUPT5H), etc. In some instances, the subject compound diminishes interaction of the SPT4 protein and a second protein. In certain instances, the second protein is a SPT5 protein. The term SPT5 protein is used herein to collectively refer to not only yeast Spt5 proteins, but also mammalian homologs thereof, e.g., human SUPT5H; murine Supt5h, etc. In certain embodiments of the method, the subject compound diminishes interaction between Supt4h and Supt5h. Human Supt4h may form a complex with Supt5h as may its yeast ortholog to regulate transcription elongation (Guo et al., "Core structure of the yeast spt4-spt5 complex: a conserved module for regulation of transcription elongation," Structure (2008) 16: 1649-1658; Hatzog et al., "Evidence that Spt4, Spt5, and Spt6 control transcription elongation by RNA polymerase II in *Saccharomyces cerevisiae*," Genes Dev. (1998) 23:357-369; Wada et al., "DSIF, a novel transcription elongation factor that regulates RNA polymerase I processivity, is composed of human Spt4 and Spt5 homologs," Genes Dev (1998) 12: 343-356; Wenzel et al., "Crystal structure of the human transcription elongation factor DSIF hSpt4 subunit in complex with the hSpt5 dimerization interface," Biochem J (2009) 425: 373-380). In certain embodiments of the method, the compound diminishes interaction between Supt5h and RNA polymerase II. For example, a subject compound may interfere with binding of Supt 5h to RNA polymerase II, and its effects on the interaction between Supt4h and Supt5h may be indirect.

Also provided are methods of diminishing interaction of a SPT4 protein (e.g., as described herein) and a second protein in a sample by contacting the sample with an effective amount of a compound (e.g., as described herein) that differentially, if not selectively, diminishes the interaction of the SPT4 protein and the second protein. In certain instances, the second protein is a SPT5 protein (e.g., as described herein). By "diminishes interaction" is meant that the extent of binding of the SPT4 protein to the second protein (e.g., a fraction of bound SPT4 as compared to total SPT4) is reduced by 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more, e.g., as compared to a suitable control, e.g., a cell not contacted with the compound. Any convenient methods may be utilized to determine extent of binding of the SPT4 protein to the second protein. In certain embodiments of the method, the compound diminishes interaction between Supt4h and Supt5h. The compound may specifically bind to the SPT4 protein and disrupt the interaction of the SPT4 protein with the SPT5 protein. In some instances, the compound specifically binds to the SPT5 protein and disrupts the interaction between the SPT4 and SPT5 protein.

In some instances, an effective amount of a compound is an interaction diminishing amount, i.e., an amount of the compound that inhibits the formation of a SPT4 complex (e.g., a SPT4/SPT5 complex) by 20% or more, such as 30% or more, 40% or more, 50% or more, 60% or more, 70% or more, 80% or more, or even 90% or more, as compared to SPT4 complex formation in the absence of the compound. Any convenient methods of assaying inhibition of complex formation or competitive inhibition may be utilized, such as those methods described by Cheng et al. "Selective reduction of the deleterious activity of extended tri-nucleotide repeat containing genes" WO 2012078906, the disclosure of which assay methods are herein incorporated by reference.

Any convenient cells may be targeted for use in the subject methods. In some instances, the types of cells in which the compound exhibit activity are ones that include a target gene containing a mutant extended trinucleotide repeat. In some embodiments of the method, the cell is an animal cell or a yeast cell. In certain instances, the cell is a mammalian cell.

In practicing methods according to certain embodiments, an effective amount of the compound, e.g., SPT4 modulatory agent, is provided in the target cell or cells. In some instances, the effective amount of the compound is provided in the cell by contacting the cell with the compound. Contact of the cell with the modulatory agent may occur using any convenient protocol. The protocol may provide for in vitro or in vivo contact of the modulatory agent with the target cell, depending on the location of the target cell. In some instances, the cell is in vitro. In certain instances, the cell is in vivo. Contact may or may not include entry of the compound into the cell. For example, where the target cell is an isolated cell and the modulatory agent is an agent that modulates expression of SPT4, the modulatory agent may be introduced directly into the cell under cell culture conditions permissive of viability of the target cell. The choice of method is generally dependent on the type of cell being contacted and the nature of the compound, and the circumstances under which the transformation is taking place (e.g., in vitro, ex vivo, or in vivo).

Alternatively, where the target cell or cells are part of a multicellular organism, the modulatory agent may be administered to the organism or subject in a manner such that the compound is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are in some cases returned to a living body.

In certain embodiments, the method is an in vivo method that includes: administering to a subject in need thereof an effective amount of a subject compound that selectively reduces the deleterious impact of the target gene to modify progression of a disease arising from the target gene in the subject. The term "treating" or "treatment" as used herein means the treating or treatment of a disease or medical condition in a patient, such as a mammal (such as a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered can be determined using any convenient methods to be an amount sufficient to produce the desired effect in association with a pharmaceutically acceptable diluent, carrier or vehicle. The specifications for the unit dosage forms of the present disclosure will depend on the compound and the effect to be achieved, and the pharmacodynamics associated with the compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the subject compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a mutant extended nucleotide repeat (NR) containing target gene. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein).

In some embodiments, the method includes obtaining a biological sample from the subject and assaying the sample, e.g., for the presence of a target gene or gene product or for the presence of cells that are associated with the disease or condition of interest (e.g., as described herein). The sample can be a cellular sample. In some cases, the sample is a biopsy. The assessment step(s) of the subject method can be performed at one or more times before, during and/or after administration of the subject compounds, using any convenient methods. In certain cases, the assessment step includes identification of cells including a mutant extended nucleotide repeat (NR) containing target gene. In certain instances, assessing the subject includes diagnosing whether the subject has a disease or condition of interest.

In some instances, the method delays occurrence of a symptom associated with the disease. In certain instances, the method reduces the magnitude of a symptom associated with the disease. Disease conditions of interest include those associated with the deleterious activity of genes containing mutant extended trinucleotide repeat domains. The term "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition). Specific disease conditions in which the methods and compositions of the invention find use include, but are not limited to, those listed in the Introduction section above, and include polyQ disease conditions, such as Spinocerebellar ataxia type 1, Spinocerebellar ataxia type 2, Spinocerebellar ataxia type 3, Spinocerebellar ataxia type 7, Spinocerebellar ataxia type 17, Dentatorubral pallidoluysian atrophy, spinobulbar muscular atrophy, and Huntington's Disease; other trinucleotide repeat diseases, e.g., Fragile X syndrome, Fragile XE MR, Fragile X tremor/ataxia syndrome (FXTAS), myotonic dystrophy, Friedreich's ataxia, spinocerebellar ataxia 8 (SCA8), and spinocerebellar ataxia 12 (SCA12); polyalanine expansion disorders, e.g., myotonic dystrophy type 2, spinocerebellar ataxia 10, spinocerebellar ataxia 31, progressive myoclonic epilepsy; hexanucleotide repeat disease conditions, e.g., autosomal-dominant frontotemporal dementia (FTD) and amyotrophic lateral sclerosis (ALS); and the like.

The term "surrogate marker" is employed in its conventional sense to refer to a measure of the effects of specific disease treatment or predict outcomes in a clinical trial. Surrogate markers can be defined as a laboratory measurement or a physical sign that is used in therapeutic trials as a substitute for a clinically meaningful endpoint. Reliable surrogates, rigorously validated in phase III clinical trials, can forecast the long term effect of the therapy based on how the patient feels, functions, or survives (Katz, "Biomarkers and Surrogate Markers: an FDA Perspective," NeuroRx (2004) 1: 189-95). These markers may also be used to compare drug efficacy between trials and may even become the basis for which new drugs gain regulatory approval for marketing (Twaddell, "Surrogate outcome markers in research and clinical practice," Australian Prescriber (2009) 32: 47-50). Because their use can reduce the size, duration, and cost of large studies or clinical trials, these markers are especially valuable if the predicted drug effect prevents death or promotes other critically important outcomes. For some progressive diseases, surrogate markers may be able to determine the disease stage (Weston, "The use of surrogate end points in cardiovascular disease and diabetes," The British Journal of Cardiology (2008) 15: S6-S7). Depending on the specific disease condition, surrogate markers may vary widely. Embodiments of the present disclosure therefore include administering a compound, e.g., as described herein, to modulate, e.g., improve, one or more surrogate markers of the disease condition.

For example, where the target disease condition being treated is Huntington's Disease, a variety of different surrogate markers may be employed to monitor the disease and the effect of therapy thereon. In some instances, a surrogate marker that may evaluated includes mutant Huntingtin proteins, DNAs or RNAs and a protocol may include assaying for one or more of these markers. A protocol considered a standard method of assessing the clinical features and course of Huntington's Disease is the Unified Huntington's Disease Rating Scale (UHDRS). The method evaluates Huntington's Disease patients in four areas: motor function, cognitive function, behavioral abnormalities and functional capacity. The motor section provides a scale ranging from 0 to 4 for rating oculomotor function, dysarthria, chorea, dystonia, gait, and postural stability. A higher total score indicates more severe motor impairment. Next, a patient's cognitive function is assessed with three tests, which are a phonetic verbal fluency test, the Symbol Digit Modalities Test, and the Stroop Interference Test. Here, higher raw scores from each test indicate better cognitive performance. The behavioral portion of the protocol measures the frequency and severity of abnormalities in mood, behavior, and psychosis with a scale ranging from 0 to 4, with 0 representing an absence of a behavior and 4 representing a severe manifestation of a behavior. The total behavior score is the sum of all responses, and a higher score indicates a greater severity of behavioral symptoms. The behavioral section also prompts the evaluator to determine if the patient shows evidence of confusion, dementia, or depression. Incorporating radiographic measures of disease progression, the functional assessments include the total functional capacity score, the independence scale, and a checklist of tasks. The total functional capacity score derives from a scale ranging from 0 to 2 or 3, with 0 representing an inability to operate normally and 2 or 3 representing normal functional capacity. The independence scale ranges from 0 to 100, with each increment of 10 representing a decreased need for special care, assistance, and supervision. The checklist of questions regarding the patient's ability to carry out a task is summed by giving a score of 1 to all "yes" replies. Higher scores represent better patient functioning than lower scores (Kieburtz, et al., "Unified Huntington's Disease Rating Scale: Reliability and Consistency," Movement Disorders (1996) 11: 136-42). Practice of embodiments of the methods results in improvement in one or more, including all of the UHDRS parameters, where the improvement in some instances is 5% or greater, such as 10% or greater, and in some instances may be 100%, or even greater.

Results from other behavioral and task completion tests may serve as surrogate markers for Huntington's Disease in embodiments of the present disclosure. The Reading the Mind in the Eyes Test (RMET), for instance, is a surrogate measure of amygdala function that is clinically useful across all disease stages in Huntington's. It is based on an individual's ability to understand the presence of beliefs, feelings, intentions and interest in other people that can differ from their own or from reality. Patients are shown a picture of the eyes and are asked to determine which of four emotional/mental state words positioned around the picture best captures the thoughts or feelings portrayed in the eyes. Performance on this test, determined by the total number of correct responses, was found to correlate negatively with proximity to disease onset and became progressively worse with each stage of disease (Mason, et al., "The role of the amygdala during emotional processing in Huntington's disease: From pre-manifest to late stage disease," Neuropsychologia (2015) 70: 80-9). Patient speech patterns have also been analyzed for use as a marker of Huntington's Disease. Patients can be asked to read a passage or produce a monologue. Research has shown patients carrying the mutant Huntingtin (Htt) gene present with slower rates of speech, take longer to say words and produce greater silences between and within words compared to healthy individuals (Vogel, et al., "Speech acoustic markers of early stage and prodromal Huntington's disease: a marker of disease onset?," Neurospychologia (2012) 50: 3273-8). Other markers include dual-task performance tests, where Huntington's Disease patients are slower and less accurate at performing simple tasks alone or together, and eye movements, which can provide information about disease severity and progression (Vaportzis, et al., "Effects of task difficulty during dual-task circle tracing in Huntington's disease," Journal of Neurology (2015) 262: 268-76), (Anderson and MacAskill, "Eye movements in patients with neurodegenerative disorders," Nature Reviews. Neurology (2013) 9: 74-85). Other markers include, but are not limited to, the Choice Reaction Task to evaluate subtle motor dysfunction, the Hopkins Verbal Learning Test to evaluate episodic memory, a computerized Mental Rotation Task to assess visuospatial processing, and a set-shifting task (Rosas, et al., "PRECREST: a phase I prevention and biomarker trial of creatine in at-risk Huntington disease," Neurology (2014) 82: 850-7), (Beste, et al., "A novel cognitive-neurophysiological state biomarker in premanifest Huntington's disease validated on longitudinal data," Sci. Rep. (2013) 3:1-8). Practice of embodiments of the methods can result in improvement in the parameters being measured in the particular test that is employed, where the improvement in some instances is 5% or greater, such as 10% or greater, and in some instances may be 100%, or even greater.

In some instances, samples taken from the blood, tissues and body fluids of Huntington's Disease patients are analyzed for surrogate markers. These markers may vary, where examples of such markers include analytes found in serum or physical measurements, such as pH or blood volume. The concentration, levels, or quantitative measurements of such markers in body fluids and tissues are often found to correspond with the emergence of Huntington's Disease symptoms. For example, increased serum levels of oxysterols such as free 24S-hydroxycholesterol and the 24S-hydroxycholesterol/total cholesterol ratio were associated with greater risk of impairment on tasks that assessed psychomotor speed and executive functioning. Meanwhile, higher levels of free 27-hydroxycholesterol and the 27-hydroxycholesterol/total cholesterol ratio were associated with greater risk of delayed memory impairment (Bandaru and Haughey, "Quantitative detection of free 24S-hydroxycholesterol, and 27-hydroxycholesterol from human serum," BMC Neuroscience (2014) 15: 137). Another example of a marker found in body fluid is cortisol, of which higher concentrations in saliva was strongly associated with reduced information encoding and memory retrieval and increased motor sign severity in pre- or early-Huntington's Disease patients (Shirbin, et al., "The relationship between cortisol and verbal memory in the early stages of Huntington's Disease," Journal of Neurology (2013) 260: 891-902). Demonstrating that physical measures may have use as surrogate markers, studies found an increase in neuronal pH and cerebral blood volume in prodromal or early-Huntington's Disease patients (Hua, et al., "Elevated arteriolar cerebral blood volume in prodromal Huntington's Disease," Movement Disorders (2014) 29: 396-401), (Chaumeil, et al., "pH as a biomarker of neurodegeneration in Huntington's disease: a translational rodent-human MRS study," Journal of Cerebral Blood Flow (2012) 32: 771-9). Yet another instance of a molecular surrogate is transcript expression, specifically the decrease after treatment in expression of genes that were initially expressed at higher levels in Huntington's Disease subjects compared to healthy individuals (Borovecki, et al, "Genome-wide expression profiling of human blood reveals biomarkers for Huntington's Disease," PNAS (2005) 102: 11023-028). Other surrogate markers in body fluids include, but are not limited to: C-reactive proteins, myeloperoxidase (MPO)/white blood cell (WBC) ratio, interleukin-6 (IL-6), thioredoxin reductase-1 (TrRd-1), thioredoxin-1 (Trx-1), and muscle adenosine triphosphate (Sanchez-Lopez, et al., "Oxidative stress and inflammation biomarkers in the blood of patients with Huntington's disease," Neurological Research (2012) 34: 721-4), (Lodi, et al., "Abnormal in vivo skeletal muscle energy metabolism in Huntington's disease and dentatorubropallidoluysian atrophy," Annals of Neurology (2000) 48: 72-6). Practice of embodiments of the methods can result in improvement in the marker(s) being measured in the particular test that is employed, where the improvement in some instances is 5% or greater, such as 10% or greater, and in some instances may be 100%, or even greater.

Additionally, surrogate markers for Huntington's Disease may be imaging markers, e.g., markers obtained by neuroimaging and magnetic resonance imaging (MRI). Imagining is employed to provide information about volume, levels of atrophy, and activity in white and grey matter across regions of the brain. As described by van den Bogaard et al., "MRI biomarkers in Huntington's Disease," Frontiers in Bioscience (2012) 4: 1910-25. Common MRI methods include structural MRI, Diffusion Tensor Imaging, Magnetization Transfer Imaging, Magnetic Resonance Spectroscopy, and Functional MRI. Structural or volumetric MRI can reveal regional, progressive thinning of the cortical ribbon and grey and white matter reductions. Structural MRI scans can also detect the amount and rates of atrophy in brain regions, especially the caudate nucleus, globus pallidus, and putamen, which appears to occur in a pre- or early-disease state. Various semi- to fully-automate techniques such as Voxel Based Morphometry (VBM), Boundary Shift Integral (BSI) and FMRIB's Integrated Registration and Segmentation Technique (FIRST) have been described (van den Bogaard, et al., "MRI biomarkers in Huntington's Disease," Frontiers in Bioscience (2012) 4: 1910-25). With Diffusion Tensor Imaging (DTI), the integrity of tissue matter is evaluated based upon the diffusion properties of protons in the intra- and extracellular space. Disturbances in fractional anisotropy (FA), Apparent Diffusion Coefficient (ADC), mean diffusivity (MD) and total diffusivity (TraceD) in white and great matter are measured during a DTI scan. An FA value close to 0 is representative of equal diffusion in all directions. In contrast, an FA value close to or equal to 1 represents highly directional diffusion. High MD-values represent unrestricted diffusion and low MD-values suggest restricted diffusion. An increase in MD and FA values in several regions of the brain collectively demonstrated selective degeneration of connections in subcortical grey and white matter, which was likely due to the death of the striatal medium-size spiny neurons in Huntington's Disease (Douaud, et al., "In vivo evidence for the selective subcortical degeneration in Huntington's disease," NeuroImage (2009) 46: 958-66), (van den Bogaard, et al., "MRI biomarkers in Huntington's Disease," Frontiers in Bioscience (2012) 4: 1910-25). Another technique, Magnetization Transfer Imaging (MTI), provides a way to examine tissue structure. The technique relies on the interaction between protons in free fluid and protons bound to macromolecules. The magnetization saturation and relaxation within macromolecules affect the observable signal. The Magnetization Transfer Ratio (MTR), representing the percentage of variation in the MR signal between the saturated and unsaturated acquisitions, is a measure used in clinical studies. Two main outcome measures, the mean MTR and the MTR peak height from histogram analysis, are reported. In a study of Huntington's Disease carriers, the MTR was significantly decreased in all subcortical structures except the putamen, revealing degeneration of the subcortical and cortical grey matter (Ginestroni, et al., "Magnetization transfer MR imaging demonstrates degeneration of the subcortical and cortical gray matter in Huntington's Disease," American Journal of Neuroradiology (2010) 31: 1807-12), (van den Bogaard, et al., "MRI biomarkers in Huntington's Disease," Frontiers in Bioscience (2012) 4: 1910-25). Yet another technique is Magnetic Resonance Spectroscopy (MRS). MRS uses hydrogen protons to measure metabolite concentrations. Unlike previous techniques, MRS gives information about changes in physiological processes. The most common metabolites examined are: N-acetylaspertate, a marker for neuronal and axonal integrity, Creatine, a marker for brain energy metabolism, Choline, a marker reflecting membrane turnover, Myo-inositol, a marker of osmolytes and astrocytes, Lactate, a marker of interruptions of oxidative processes and the beginning of anaerobic glycolysis, and glutamate, a neurotransmitter. Decreased levels of creatine and N-acetylaspertate and increased levels of lactate across different brain regions have been reported in premanifest Huntington's disease studies (van den Bogaard, et al., "MRI biomarkers in Huntington's Disease," Frontiers in Bioscience (2012) 4: 1910-25). Finally, functional MRI (fMRI) uses the blood-oxygen-level-dependent (BOLD) signal to discriminate brain regions with altered activation. Activation of a brain region requires an increase in energy and, consequently, blood demand, measured with fMRI. Different functional tasks such as a clock reading task, verbal working memory task, Simon task, or a porteus maze task can be employed during fMRI scanning. Abnormal connectivity or activation patterns are associated with premanifest and manifest Huntington's Disease. For instance, premanifest Huntington's Disease patients often show increased activation of several regions while there generally is a reduction of activation in premanifest gene carriers "close to onset" (van den Bogaard, et al., "MRI biomarkers in Huntington's Disease," Frontiers in Bioscience (2012) 4: 1910-25). According to Van den Bogaard, volumetric measures and white matter diffusion tensor imaging integrity measures are the best techniques for assessing the pre-manifest stage of Huntington's disease. For early manifest Huntington's Disease, Magnetic Transfer Imaging and measurements of whole brain atrophy are more appropriate (van den Bogaard, et al., "MRI biomarkers in Huntington's Disease," Frontiers in Bioscience (2012) 4: 1910-25). Practice of embodiments of the methods can result in improvement in the parameters being measured in the particular imaging test that is employed, where the improvement in some instances is 5% or greater, such as 10% or greater, and in some instances may be 100%, or even greater.

Separate from MRI scans, Positron Emission Tomography (PET) scans have also been employed to measure cerebral metabolic activity in premanifest Huntington's Disease patients at baseline and later in subsequent years. Metabolic brain network analysis has been increasingly used to measure the expression of characteristic spatial covariance patterns in patients experiencing neurodegeneration. Measured with [$^{18}$F]-fluorodeoxyglucose scans, metabolic network activity proved sensitive to disease progression as demonstrated by its rapid rate of progression and high expression during the clinical onset of Huntington's Disease, also called phenoconversion. Abnormal elevations in baseline metabolic activity above a certain threshold indicated a high likelihood of phenoconversion in the coming years (Tang, et al., "Metabolic network as a progression biomarker of premanifest Huntington's disease," The Journal of Clinical Investigation (2013) 123: 4076-88). A decrease in cortical glucose metabolism in the bilateral frontal, temporal and parietal cortices is also suggested as a predictor for identifying a more rapid form of disease progression in early stage Huntington's Disease patients (Shin, et al., "Decreased Metabolism in the Cerebral Cortex in Early-Stage Huntington's Disease: A Possible Biomarker of Disease Progression?," Journal of Clinical Neurology (2013) 9: 21-5). Practice of embodiments of the methods can result in improvement in the parameters being measured in the particular imaging test that is employed, where the improvement in some instances is 5% or greater, such as 10% or greater, and in some instances may be 100%, or even greater.

Beyond body fluid based markers and imaging markers, surrogate markers for Huntington's Disease include a variety of dietary, mineral accumulation, and inclusion detection measures. One study assessed the influence of adherence to a Mediterranean diet on phenoconversion and found some correlation between high consumption of dairy products with an increased risk of higher urate levels, associated with faster progression in manifest Huntington's disease (Marder, et al., "Relationship of Mediterranean diet and caloric intake to phenoconversion in Huntington's Disease," JAMA Neurology (2013) 70: 1382-8). In a separate study, iron accumulation was detected in the globus pallidus in both pre-Huntington's and symptomatic patients (Sanchez-Castaheda, et al., "Seeking Huntington's disease biomarkers by multimodal, cross-sectional basal ganglia imaging," Human Brain Mapping (2013) 34: 1625-35). Another surrogate marker involves evaluation of intra-neuronal aggregates of huntingtin protein and protein fragments containing expanded polyglutamine repeats (Sieradzan, et al., "The selective vulnerability of nerve cells in Huntington's disease," Neuropathology and Applied Neurobiology (2001) 27: 1-21), (Huang, et al., "Inducing huntingtin inclusion formation in primary neuronal cell culture and in vivo by high-capacity adenoviral vectors expressing truncated and full-length huntingtin with polyglutamine expansion," The Journal of Gene Medicine (2008) 10: 269-79). In mice, gait analysis, immunostaining with the antibody EM48, and filter trap assays were employed together to show that early nuclear accumulation of mutant huntingtin protein or protein fragments in striatal neurons correlates with later striatal degeneration and motor deficits. Striatal phenotypes, therefore, specifically demonstrate that the disease progression is hastened by a mutant huntingtin protein fragment and may serve as surrogate markers predicting onset of Huntington's Disease (Wheeler, et al., "Early phenotypes that presage late-onset neurodegenerative disease allow testing of modifiers in Hdh CAG knock-in mice," Human Molecular Genetics (2002) 11: 633-40). Immunostaining patterns of antibodies such as the monoclonal antibody 1C2, capable of detecting long stretches of glutamine residues, also have the potential to provide diagnostic assistance in the postmortem central nervous system analysis of Huntington's Disease (Herndon, et al., "Neuroanatomical Profile of Polyglutamine Immunoreactivity in Huntington Disease Brains," Journal of neuropathology and experimental neurology (2009) 68: 250-61). Practice of embodiments of the methods can result in improvement in the parameters being measured in the particular test that is employed, where the improvement in some instances is 5% or greater, such as 10% or greater, and in some instances may be 100%, or even greater.

In the subject methods, the compound (e.g., as described herein) may be administered to the targeted cells using any convenient administration protocol capable of resulting in the desired activity. Thus, the subject compound can be incorporated into a variety of formulations, e.g., pharmaceutically acceptable vehicles, for therapeutic administration. As reviewed above, the subject methods result in reduction in the deleterious activity of an extended trinucleotide repeat gene in a target cell or cells, where the target cell(s) may be in vitro or in vivo. In certain embodiments, the subject methods result in reduction in toxicity of a target gene, e.g., via a reduction in aggregation of a protein encoded thereby, in a target cell(s). In certain embodiments, the methods result in enhancement in function of a protein encoded by a target gene.

The above methods find use in a variety of different applications. Certain applications are now reviewed in the following Utility section.

Utility

The subject methods and compound compositions find use in a variety of applications in which reduction of the deleterious activity of gene containing a mutant extended trinucleotide repeat domain is desired. As such, aspects of the invention include reducing toxicity of and/or enhancing functionality of a protein encoded by such a gene, as described herein, in any subject in need thereof, e.g., a subject that has been diagnosed with a condition that can be treated by effecting one or more of the above outcomes in the subject. Of interest is use of the subject methods and compositions to modify the progression of disease conditions associated with the deleterious activity of genes containing mutant extended trinucleotide repeat domains. The phrase "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition). Specific disease conditions in which the methods and compositions of the invention find use include, but are not limited to polyQ disease conditions, such as Spinocerebellar ataxia type 1, Spinocerebellar ataxia type 2, Spinocerebellar ataxia type 3, Spinocerebellar ataxia type 7, Spinocerebellar ataxia type 17, Dentatorubral pallidoluysian atrophy, Spinal and bular muscular atrophy, amyotrophic lateral sclerosis (ALS) and Huntington's Disease.

In some instances, practice of subject methods results in treatment of a subject for a disease condition. By treatment is meant at least an amelioration of one or more symptoms associated with the disease condition afflicting the subject, where amelioration is used in a broad sense to refer to at least a reduction in the magnitude of a parameter, e.g., symptom, associated with the pathological condition being treated, such as loss of cognitive function, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition. Treatment may also manifest in the form of a modulation of a surrogate marker of the disease condition, e.g., as described above.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs and rats), and primates (e.g., humans, chimpanzees and monkeys). In some embodiments, the host is human.

Combination Therapies

The subject compound can be administered to a subject alone or in combination with an additional, i.e., second, active agent. As such, in some cases, the subject method further comprises administering to the subject at least one additional compound. Any convenient agents may be utilized, including compounds useful for treating viral infections. The terms "agent," "compound," and "drug" are used interchangeably herein. For example, a selective SPT4 inhibitory compound can be administered alone or in conjunction with one or more other drugs, such as drugs employed in the treatment of polyQ diseases. In some embodiments, the method further includes coadministering concomitantly or in sequence a second agent. Possible second agents of interest include, but are not limited to, dopamine-depleting agents (e.g., tetrabenazine (Xenazine) or reserpine); dopamine-receptor antagonists (e.g., neuroleptic), amantadine, levetiracetam, anticonvulsants (e.g., valproic acid), antipsychotic drugs, such as risperidone, haloperidol (Haldol) and clozapine (Clozaril); antiseizure drugs, benzodiazepines (e.g., clonazepam (Klonopin)) and antianxiety drugs such as diazepam (Valium); antidepressants including such drugs as escitalopram (Lexapro), fluoxetine (Prozac, Sarafem) and sertraline (Zoloft); laquinimod, pridopidine, rasagiline, a pan-PPAR agonist (e.g., bezofibrate); nucleic acid silencing agents, e.g., RNA silencing agents targeting, e.g., a HTT single nucleotide polymorphism (SNP); and the like. Antisense oligonucleotides or interfering RNAs directed against SUPT4H may also be part of a combination therapy. Second active agents of interest include, but are not limited to any convenient drugs that find use against a neurodegenerative condition or disease, such as Huntington's disease or amyotrophic lateral sclerosis (ALS).

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and the subject compound.

In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

In some cases, the second active agent is a nucleoside agent. Nucleoside agents of interest include any convenient agents that reduce the deleterious activity of a mutant extended trinucleotide repeat containing target gene in a cell. As used herein, the term "nucleoside agent" is meant to include both phosphorus containing agents (e.g., nucleoside agents that include O-phosphate substituted sugar moieties) and agents that lack a phosphorus moiety. Nucleosides agent of interest may include any convenient modifications to the sugar moiety, e.g., modifications where a naturally occurring hydroxyl group is replaced with a halogen atom or an aliphatic group, or is functionalized as an ether, an amine, or the like. A nucleoside agent may contain one or more protecting groups (e.g. a hydroxyl protecting group, a bidentate diol protecting group, or a heterocyclic base protecting group) independently attached to any moiety(s) of the nucleoside agent.

Any convenient nucleoside agents may find use in the subject methods and compositions. Such nucleoside agents may be assessed, among other ways, by employing the screening methods described by Cheng et al. "Selective reduction of the deleterious activity of extended tri-nucleotide repeat containing genes" WO 2012078906, the disclosure of which screening method is herein incorporated by reference. Nucleoside agents of interest include, but are not limited to, 5-fluorouracil (5-FU), 5-FU prodrugs including tegafur and 5'-deoxyfluorouridine, fluorouridine, 2'-deoxyfluorouridine, prodrug derivatives of fluorouridine or 2'-deoxyfluorouridine, fluorocytosine, trifluoro-methyl-2'-deoxyuridine, arabinosyl cytosine, prodrugs of arabinosyl cytosine, cyclocytidine, 5-aza-2'-deoxycytidine, arabinosyl 5-azacytosine, 6-azacytidine, N-phosphonoacetyl-L-aspartic acid (PALA), pyrazofurin, 6-azauridine, azaribine, thymidine, 3-deazauridine, triacetyluridine, ethoxycarbonyluridine, triacetylcytidine, cyclocytidine, 5-aza-2'-deoxycytidine, arabinosyl 5-azacytosine, 6-azacytidine, benzylacyclouridine, benzyloxybenzylacyclouridine, aminomethyl-benzylacyclouridine, aminomethyl-benzyloxybenzylacyclouridine-, hydroxymethyl-benzylacyclouridine, hydroxymethyl-benzyloxybenzylacyclouridine, 2,2'-anhydro-5-ethyluridine, 5-benzyl barbiturate, 5-benzyloxybenzyl barbiturate, 5-benzyloxybenzyl-1-[(1-hydroxy-2-ethoxy)m-ethyl] barbiturate, 5-benzyloxybenzylacetyl-1-[(1-hydroxy-2-ethoxy)methyl] barbiturate, 5-methoxybenzylacetylacyclobarbiturate, 5-ethynyluracil, bromovinyluracil, cyanodidhydropyridine, uracil, thymine, thymidine and benzyloxybenzyluracil. Any convenient prodrugs of the subject nucleoside agents may be utilized in the subject methods. Prodrugs are frequently, although not necessarily, pharmacologically inactive until converted to the active agent. In some instances, the nucleoside agent is a ribonucleoside agent selected from a 6-deazapurine ribonucleoside and a 6-azauridine ribonucleoside, as described by Cohen et al. in WO 2016/196012, the disclosure of which is herein incorporated by reference.

Also provided are pharmaceutical preparations of the subject compound and the second active agent. In pharmaceutical dosage forms, the compound may be administered in the form of a pharmaceutically acceptable salt, or the compound may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the compound composition, the severity of the symptoms and the susceptibility of the subject to side effects. Dosages for a subject compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific compound, the nature of the delivery vehicle, and the like. Preferred dosages for a subject compound or agent are readily determinable by those of skill in the art by a variety of means.

Kits & Systems

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. In some embodiments, the subject system or kit includes a dose of a subject compound (e.g., as described herein) and a dose of a second active agent (e.g., as described herein) in amounts effective to treat a subject for a disease or condition associated with the deleterious activity of a mutant extended nucleotide repeat containing target gene.

In certain instances, the second active agent is selected from: a nucleoside agent (e.g., as described herein), a dopamine-depleting agent (e.g., tetrabenazine or reserpine), a dopamine-receptor antagonist (e.g., neuroleptic), amantadine, levetiracetam, an anticonvulsant (e.g., valproic acid), a benzodiazepine agent (e.g., clonazepam), laquinimod, pridopidine, rasagiline, a pan-PPAR agonist (e.g., bezofibrate), an antipsychotic agent (e.g., risperidone or haloperidol) and a RNA silencing agent targeting a HTT single nucleotide polymorphism (SNP). Kits and systems for practicing the subject methods may include one or more pharmaceutical formulations. As such, in certain embodiments the kits may include a single pharmaceutical composition, present as one or more unit dosages, where the composition may include one or more active agents (e.g., as described herein). In some embodiments, the kit may include two or more separate pharmaceutical compositions, each containing a different active agent, at least one of which is a nucleoside compound (e.g., as described herein).

Also of interest are kits and systems finding use in the subject methods, e.g., as described above. Such kits and systems may include one or more components of the subject methods, e.g., nucleoside agents, cells, vectors encoding proteins of interest, enzyme substrates, dyes, buffers, etc. The various kit components may be present in the containers, e.g., sterile containers, where the components may be present in the same or different containers.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXAMPLES

Example 1: Synthesis of HD143 Enantiomers (R)-(+) and (S)-(−)-N-Benzyl-6-bromo-2,3,4,9-tetrahydro-1H-carbazol-1-amine hydrochloride

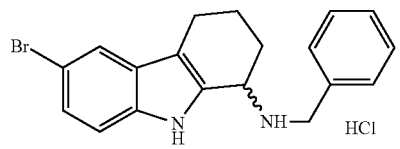 [SMILES: Brc1ccc2[nH]c3c(c2c1)CCCC3NCc1ccccc1 ; Cl]

Synthesis of 2-[2-(4-bromophenyl)hydrazinylidene]cyclohexan-1-one (A)

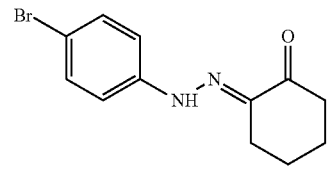

p-Bromophenylhydrazine hydrochloride (854 g, 4.0 mol, 1 equiv.) was added portion-wise to a stirred solution of cyclohexane-1,2-dione (450 g, 4.0 mol) in water (3 L) at 0-5° C. Concentrated (37%) hydrochloric acid (2 L) was then added slowly and the resultant mixture was stirred at 5-10° C. Once TLC analysis indicated disappearance of cyclohexane-1,2-dione, the mixture was cooled to 0-5° C. and the wet solid (1127 g) was obtained by filtration.

Synthesis of
6-bromo-2,3,4,9-tetrahydro-1H-carbazol-1-one (B)

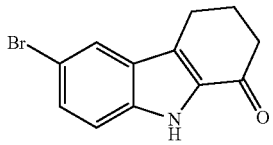 [SMILES: O=C1CCCc2c1[nH]c1ccc(Br)cc21]

A solution of A (1127 g, used as wet) in methanol (4 L) was added drop-wise to a stirred mixture of acetic acid (4 L) and concentrated hydrochloric acid (1.8 L, 37%) at 60° C. After 3 hours, TLC analysis indicated disappearance of A. The mixture was cooled to room temperature, filtered, and the filter cake was washed with methanol (1 L). The obtained solid was dried under infrared light to afford B (521 g, 49.2% yield) as a yellow solid.

$^1$H-NMR (400 MHz, DMSO); δ (ppm)=11.80 (s, 1H), 7.91 (s, 1H), 7.42-7.34 (m, 2H), 2.95 (m, 2H), 2.55 (m, 2H), 2.13 (m, 2H). MS (EI): m/z 265 [M+H]+.

Synthesis of N-benzyl-6-bromo-2,3,4,9-tetrahydro-1H-carbazol-1-amine (HD143)

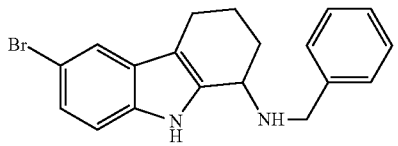 [SMILES: Brc1ccc2[nH]c3c(c2c1)CCCC3NCc1ccccc1]

Titanium(IV) isopropoxide (431 g, 1.5 mol, 2.0 equiv.) was added dropwise to a stirred solution of B (200 g, 0.76 mol) and benzylamine (122 g, 1.5 mol, 2.0 equiv.) in THF (3 L) at 0-5° C. The mixture was then stirred at 15° C. for 4 hours. Sodium borohydride (57.3 g, 1.5 mol, 2.0 equiv.) was added and the mixture was stirred at room temperature for 4 hours. Once TLC analysis indicated disappearance of B, the reaction mixture was cooled to 0-5° C. and titrated with 4N NaOH until pH reached 8-9. Filtrate was collected and the organic phase was isolated and dried over anhydrous sodium sulfate. After filtration, the solution was concentrated to afford HD143 (269 g, 100% yield) as a yellow oil.

$^1$H-NMR (400 MHz, DMSO); δ (ppm)=11.35 (s, 1H), 9.49 (dd, 2H), 7.71 (s, 1H), 7.62 (m, 2H), 7.45 (m, 3H), 7.28 (m, 1H), 4.68 (m, 1H), 4.35 (m, 2H), 2.74 (m, 2H), 2.21 (m, 2H), 2.12 (m, 1H), 1.82 (m, 1H). MS (EI): m/z 356 [M+H]+.

Preparation of (R)-(+)-N-Benzyl-6-bromo-2,3,4,9-tetrahydro-1H-carbazol-1-amine hydrochloride ((R)-(+)-HD143 HCl) and (S)-(−)-N-Benzyl-6-bromo-2,3,4,9-tetrahydro-1H-carbazol-1-amine Hydrochloride ((S)-(−)-HD143 HCl)

HD143 (8.6 g) was dissolved in methanol (250 mL) and the solution was eluted through a supercritical fluid chromatography (SFC) and the fractions that contain each of the enantiomers were collected. The SFC separation method is as follows:

| | |
|---|---|
| Instrument | Waters SF0200 |
| Column | Chiral Pak OJ, 250 × 30 mm, 5 μm |
| Mobile phase | A: Carbon dioxide; B: ethanol with 0.1% ammonium; A:B = 70:30 (v:v) |
| Flow rate | 70 mL/minute |
| Back pressure | 100 bar |
| Column temperature | 38° C. |
| Wavelength | 220 nm |
| Cycle time | 16 minutes |
| Injection volume | 5 mL per injection |

The fractions collected were combined and concentrated by rotary evaporation at 40° C. HCl in ethyl acetate (3 N, 40 mL) was added to the evaporation residue and the resultant mixture was stirred at 0-5° C. for 2 hours. The solid was isolated by filtration and washed with ethyl acetate and dried under infrared light to afford one enantiomer from the first fractions (3.9 g, 41% yield) and the other enantiomer from the second fractions (4.2 g, 44% yield).

Chiral purity and optical rotation. The enantiomer from the first fractions has chiral purity of 99.4% e.e. and an optical rotation of $[α]_D^{25}$=−34.67° (c 1.215, methanol). It is assigned as (−)-HD143. The enantiomer from the second fractions has chiral purity of 98.7% e.e. and an optical rotation of $[α]_D^{25}$=36.02° (c 1.315, methanol). It is assigned as (+)-HD143.

$^1$H-NMR (400 MHz, DMSO) for (−)-HD143; b (ppm)=11.69 (s, 1H), 9.89-9.74 (dd, 2H), 7.70-7.67 (m, 3H), 7.46-7.38 (m, 4H), 7.27-7.25 (m, 1H), 4.69 (s, 1H), 4.30 (s, 2H), 2.68 (m, 2H), 2.24 (m, 2H), 2.10 (m, 1H), 1.82 (m, 1H). MS (ES): m/z 355 [M]+.

$^1$H-NMR (400 MHz, DMSO) for (+)-HD143; m, 4H), 7.27-7.25 (m, 1H), 4.69 (s, dd, 2H), 7.69-7.67 (m, 3H), 7.46-7.38 (m, 4H), 7.27-7.25 (m, 1H), 4.69 (s, 1H), 4.29 (s, 2H), 2.68 (m, 2H), 2.24 (m, 2H), 2.08 (m, 1H), 1.82 (m, 1H). MS (ES): m/z 355 [M]+.

Structure Determination of (+)-HD143
Single Crystal Growth

Block-like single crystals of the (+)-HD143 hydrochloride used for SCXRD characterization were crystallized from MeOH/ACN (1:10, v/v) solvent mixture by slow evaporation method. The experimental details are elaborated below.

First, 3.6 mg compound (+)-HD143 hydrochloride starting material was weighed into a 3-mL vial and then 0.45 mL MeOH/ACN(1:10, v/v) solvent mixture was added. After being oscillated on a vortex and ultrasonically shaken to accelerate dissolution, the suspension was filtered through PTFE filter membrane (0.45 μm) and disposable syringe to a 4-mL shell vial (44.6 mm×14.65 mm). A crystal sample was added to the vial as crystal seed and the vial was then covered with transparent PE-Plug in which one pinhole was produced. After 1 day, block-like single crystals were obtained.

Single Crystal Structure Determination

A suitable single crystal with good diffraction quality was selected from the block-like crystal samples and was analyzed by single-crystal X-ray diffractometry. The structure of the crystal was determined successfully. The crystal system is monoclinic and the space group is P2$_1$. The cell parameters are: a=9.5518(12) Å, b=7.6911(9) Å, c=11.8400 (15) Å, α=90°, β=95.224(4)°, γ=90°, V=866.20(18) Å3. The formula weight is 391.73 g·mol-1 with Z=2, resulting in the calculated density of 1.502 g·cm-3. Further crystallographic data and the refinement parameters are listed in Table 2.

As shown in FIG. 5A, the asymmetric unit of the single crystal structure is comprised of one (+)-HD143 cation and one chloride ion. The thermal ellipsoids drawing of the compound (+)-HD143 cation and chloride ion in the crystal lattice is shown in FIG. 5B. The single crystal structure determination confirmed that the stereochemistry structure of the compound (+)-HD143 hydrochloride is consistent with the (R) configuration of the chemical structure as shown in FIG. 5C.

The absolute configuration assignment (R/S) of the chiral atom in the (+)-HD143 hydrochloride is {C1(R)}. The Flack parameter was refined to 0.037(4). Determination of absolute structure using Bayesian statistics on Bijvoet differences using the PLATON results in (Hooft y=0.037(2); P2(true)=1.000, P3(true)=1.000, P3(rac-twin)=0.0E+00, P3(false)=0.0E+00, corr.coeff=0.999). Note: (1). The Flack parameter x (μ) is used to determine chirality of the crystal studied. There are conditions under which one may say that the absolute structure of the crystal (or the absolute configuration of the compound) has been determined satisfactorily. Firstly the standard uncertainty μ of the Flack parameter x (μ) is sufficiently small: in general μ should be less than 0.04 but this value may be relaxed to 0.10 for a compound proven by other means to be enantiomerically pure. Secondly the value of the Flack parameter itself should be close to zero within a region of three standard uncertainties i.e. μ<0.04 (or μ<0.10 for a chemically proven enantiomeric excess of 100%) and |x|/μ<3.0, in general|x|<0.1. (Reference: H. D. Flack and G. Bernardinelli. *CHIRALITY*. (2008). 20, 681-690.) (2). Bayesian statistics on Bijvoet differences is another method to determinate the absolute structure (Reference: Rob Hooft, Leo Straver and Anthony Spek. *J. Appl. Cryst*. (2008). 41, 96-103). This method not only gives a qualitative assignment of the absolute structure, but also a quantitative estimate of the reliability of that assignment. (A pair of values P2 (true) and P2 (false) expressing the likelihood that the given absolute structure is right or wrong, assuming the prior knowledge that the compound is enantiopure. A triplet of values P3 (true), P3 (rac-twin) and P3 (false) expressing the likelihood that the given absolute structure is right, that the crystal is a 50%/50% inversion twin, or that the absolute structure should be inverted. This assumes the prior knowledge that the crystal cannot be an inversion twin with another ratio.)

TABLE 2

Crystallographic data and refinement parameters

| | |
|---|---|
| Empirical formula | $C_{19}H_{20}BrClN_3$ |
| Formula weight | 391.73 |
| Temperature | 173.13K |
| Wavelength | Mo/Kα (λ = 0.71073) |
| Crystal system, space group | monoclinic, P2$_1$ |
| Unit cell dimensions | a = 9.5518(12) Å |
| | b = 7.6911(9) Å |
| | c = 11.8400(15) Å |
| | α = 90° |
| | β = 95.224(4)° |
| | γ = 90° |
| Volume | 866.20(18) Å$^3$ |
| Z, Calculated density | 2, 1.502 g/cm$^3$ |
| Absorption coefficient | 2.528 mm$^{-3}$ |
| F(000) | 400.0 |
| Crystal size | 0.25 × 0.18 × 0.10 mm$^3$ |
| 2 Theta range for data collection | 5.742° to 55.132° |
| Limiting indices | −12 ≤ h ≤ 12 |
| | −10 ≤ k ≤ 9 |
| | −15 ≤ l ≤ 15 |
| Reflections collected/Independent reflections | 20684/3967 [R$_{int}$ = 0.0415, R$_{sigma}$ = 0.0413] |
| Refinement method | Full-matrix least-squared on F$^2$ |
| Data/restraints/parameters | 3967/1/220 |
| Goodness-of-for on F$^2$ | 1.009 |
| Final R indices [I ≥ 2 sigma(I)] | R$_1$ = 0.0269, wR$_2$ = 0.0556 |
| Final R indices [all data] | R$_1$ = 0.0329, wR$_2$ = 0.0574 |
| Largest diff. peak and hole | 0.22/−0.40 e.Å$^{-3}$ |
| Flack parameter | 0.037(4) |
| Bayesian statistics on Bijvoet differences[1] | Hooft y = 0.03792), P2(true) = 1.00, P3(true) = 1.000, P3(rae-twin) = 0.0E+00, P3(false) = 0.0E+00, corr.coef = 0.999 |

[1]Analyzed by PLATON program (version 191017)

Example 2: Activity of HD143 Enantiomers

A. Materials and Methods
1. Slit *Gaussia* Luciferase Complementation Assay
   a. Plasmid Construction
   i pNBR-X1-Supt4-Gluc1 and pNEBR-X1-NGN-Guc2
   The HA-Supt4hand Flag-NGN fragments are amplified by PR using the plasmid pHA-Supt4h-YC and pFlag-NGN-YN and sub-cloned individually into pcDNA3.1-Gluc1 and pcDNA3.1-Gluc2 (described in "A highly sensitive protein-protein interaction assay based on Gausssia Luciferase" published at Nat Methods. 2006 December; 3(12):977-9.Epub 2006 Nov. 12). Then HA-Supt4h-Gluc1 and Flag-NGN-Gluc2 are amplified by PCR and inserted to pNEBR-X1-Hygro (New England BioLabs), which contain RheoSwitch responsive element under the control of Rheo-Switch ligand.
   ii: pNEBR-X1-Supt4h-G1-NGN-G2
   PCR products containing the sequence from 5XRE to polyA in pNEBR-X1-NGN-G2 are inserted to pNEBR-X1-Supt4h-G1 at Pcil site to generate Supt4h-G1 and NGN-G2 bidirectional under their own RheoSwitch responsive element and polyA in the same plasmid.
   b. Stable Cloned Cell Line
   i: 293-R1 is a cloned cell which is engineered to constitutively express RSL1 receptor/activator by transfecting HEK 293 cells with pNEBR-R1 plasmid (New England BioLabs) and selected with Blasticidin.
   ii: M2-8 is a cloned 293-R cell which can inducibly express pNEBR-X1-Supt4h-G1-NGN-G2 by addition of RSL1. Two point mutations (M431 and M1101) are introduced to the GL1 and GL2 for better stability according to "A high-throughput cell-based *Gaussia* luciferase reporter assay for identifying modulators of fibulin-3 secretion" published on J Biomol Screen. 2013 July; 18(6):647-58. The cell line is selected by Hygromycin.
   c. Cell Culture and Transfection Condition
   All the HEK-293 cells and derivative cell clones are maintained in DMEM containing 10% FBS plus corresponding antibiotics (250 μg/ml hygromycin B, 10 μg/ml blasticidin or both) at 37° C., 5% $CO_2$.
   d. Bioluminescence Assay in Cell Lysates
   For stable cell M2-8, the cells are plated into 96 well white plate directly. 24 hours later, RheoSwitch ligand together with/without test compound is added to the cells for induction/drug treatment. After 24 hr, the cells are washed with PBS and the plate was put in −20° C. freezer for overnight. After taking out the plate from freezer, lysis buffer (30 mM Tris-HCl, pH 8.0, 5 mM NaCl, 0.1% Triton X-100) with 10 μg/ml native coelenterazine (Nanolight Technology) is immediately added to the cells. The cells are lysed at room temperature for one hour in dark. After shaking for about 1 min, the signal intensities (integrated 100 ms) from the plate were read on Tecan Infinite M200 or M1000.

2. Cellular Toxicity Assay in M2-8 Cells

The cell viability is determined by CellTiter-Glo 2.0 Assay (G9242 from Promega), which measures ATP, a key indicator of cell health. After 24-hour treatment with compounds to M2-8 cells in a 96 well white plate, the same amount as the media of CellTiter-Glo reagent is added to the wells and mixed well. Then after 10 minutes incubation at room temperature, the luminescence signal intensities (integrated 100 ms) were read on Tecan Infinite M200.

3. Mutant HTT Activity Assay in Induced Pluripotent Stem Cells (iPSC)

Huntington disease patient iPSCs (ND36999 from Coriell Institute) were detached into single cells by Accutase (AT104 from Accutase) and plated on a 24-well plate coated with Matrigel (354277 from Corning). When the cells' confluency reaches about 70%, compounds are added to the cell culture medium StemMACS (130104368 from MiltenyiBiotec) and incubated with the cells for one day. Then the medium is removed and the cells are washed with PBS. After all liquid is removed, the plate is put in −80° C. for overnight. After taking out the plate from freezer, lysis buffer (30 mM Tris-HCl, pH 8.0, 5 mM NaCl, 0.1% Triton X-100) with complete proteinase inhibitor cocktail (5892791001 from Sigma-Aldrich) is immediately added to the cells. Cell samples are lysed on ice for 10 minutes. The supernatants from spinning (14 k rpm for 10 min) are collected. The protein concentrations are determined by BCA assay (Pierce, ThermoFisher). Equal amounts of protein are loaded onto 4-12% gel. After electrophoresis, the gels are transferred to nitrocellulose membranes by wet transfer at 35V for 16 hr. The protein level of mutant HTT, total HTT and tubulin are determined by immunoblotting with anti-poly Glutamine (MAB1574 from Millipore), anti-Huntingtin protein (MAB2166 from Millipore) and anti-alpha tubulin (AJ1034a from ABGENT). Blots are imaged on a Li-Cor Odyssey infrared imager. The bands intensities are determined by Li-Cor Odyssey software.

3. HD Lymphoblastoid Cell Assay to Assess Mutant HTT Reduction a. Compound Treatments Lymphoblastoid cells GM14044, which are derived from Juvenile HD patient with around 250 CAG repeats in the mutant HTT allele, are used for lymphoblastoid cell assays. Lymphoblastoid cells are cultured as suspension cells. Right before the compound treatments, $5\times10^5$ cells/well are seeded into 24 well plate in 1.5 ml RPMI culture medium plus 10% fetal bovine serum. Compounds in serial dilutions are added into the well for the indicated final concentration. Cells are maintained in 37° C., 5% $CO_2$ incubator for 72 hours b. Compound Effect in Reducing mHTT ($IC_{50}$)

The rest of the cell/medium mixture is removed from culture plate into a 1.5 ml microcentrifuge tube, then centrifuged at 2500 rpm for 2 minutes to remove the culture medium. Cell pallets are washed with 1×PBS, then stored at −80° C. until ready for Western blot analysis. Western blot analysis is performed as described above. The intensity of HTT from untreated cells is set as 100% and the $IC_{50}$ of the compound is defined as the compound concentration at which the HTT protein was reduced to 50%.

B. Results

Racemic-HD143 and the enantiomeric (+)-HD143 and (−)-HD143 compounds were tested, e.g., using the methods described above, to assess their biological activity including reduction of the deleterious activity of a mutant extended nucleotide repeat (NR) containing target gene in a cell.

1. *Gaussia* Luciferase Complementation Assay

Racemic-HD143 and the enantiomeric (+)-HD143 and (−)-HD143 compounds were tested in a split *Gaussia* luciferase complementation assay, according to the methods described above. A graph of the data is shown in FIG. 1. (+)-HD143 is 2 fold more potent than racemic HD143 ($IC_{50}$=15 nM vs. $IC_{50}$=30 nM), while (−)-HD143 is much less active ($IC_{50}$=900 nM). This result indicates that (+)-HD143 is the active component of racemic HD143.

2. Cell Viability

Figure 2:
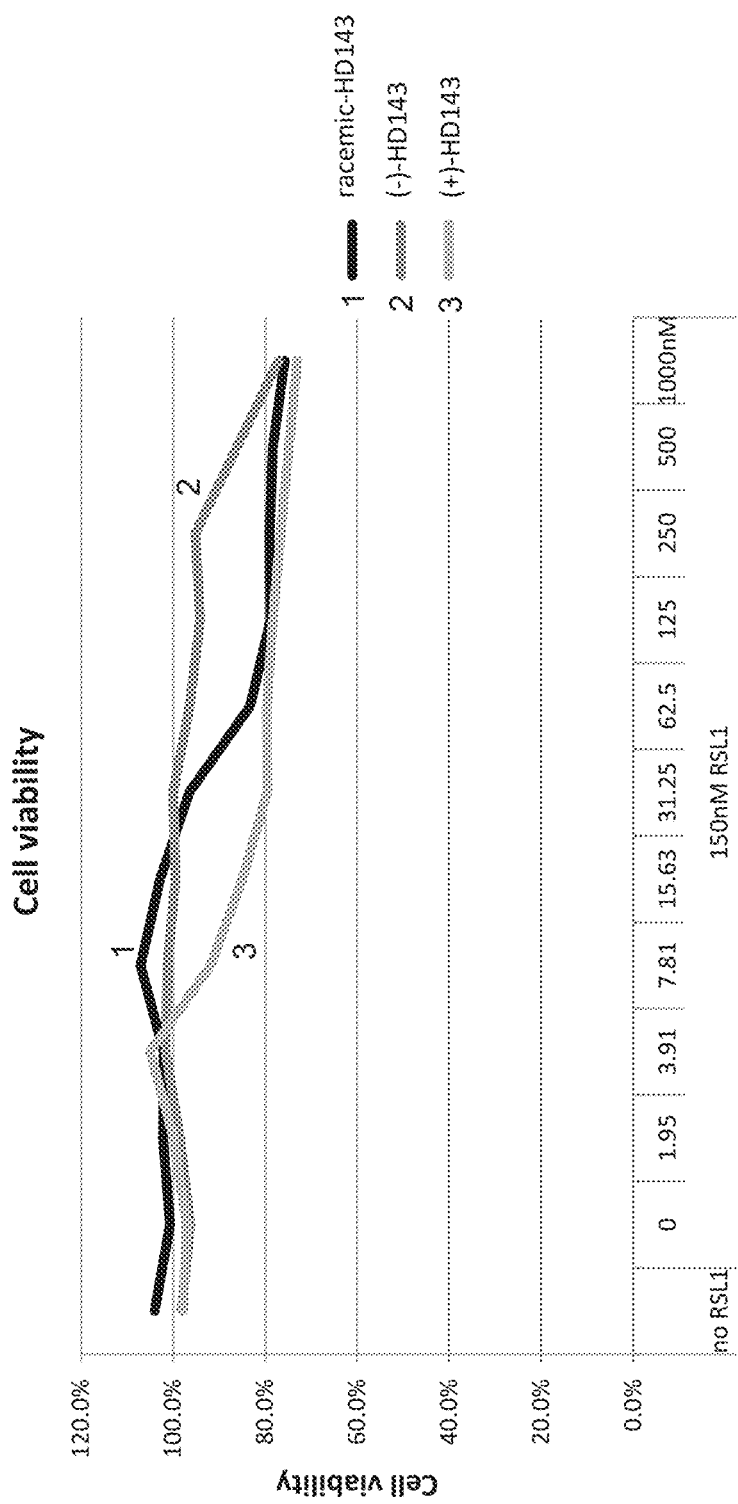
FIG. 2 shows cell viability results for racemic-HD143 versus the (S)-(–)-HD143 and (R)-(+)-HD143 enantiomers as tested in a cell viability assay, as reported in the Experimental Section, below.

The cytotoxicities of racemic-HD143 and the enantiomeric (+)-HD143 and (−)-HD143 compounds were tested in a cell viability assay, according to the methods described above. A graph of the data is shown in FIG. 2 which indicates that each of the three compositions had a $LD_{50}$ of >1000 nM.

3. Mutant HTT Activity Assay

Figure 3:
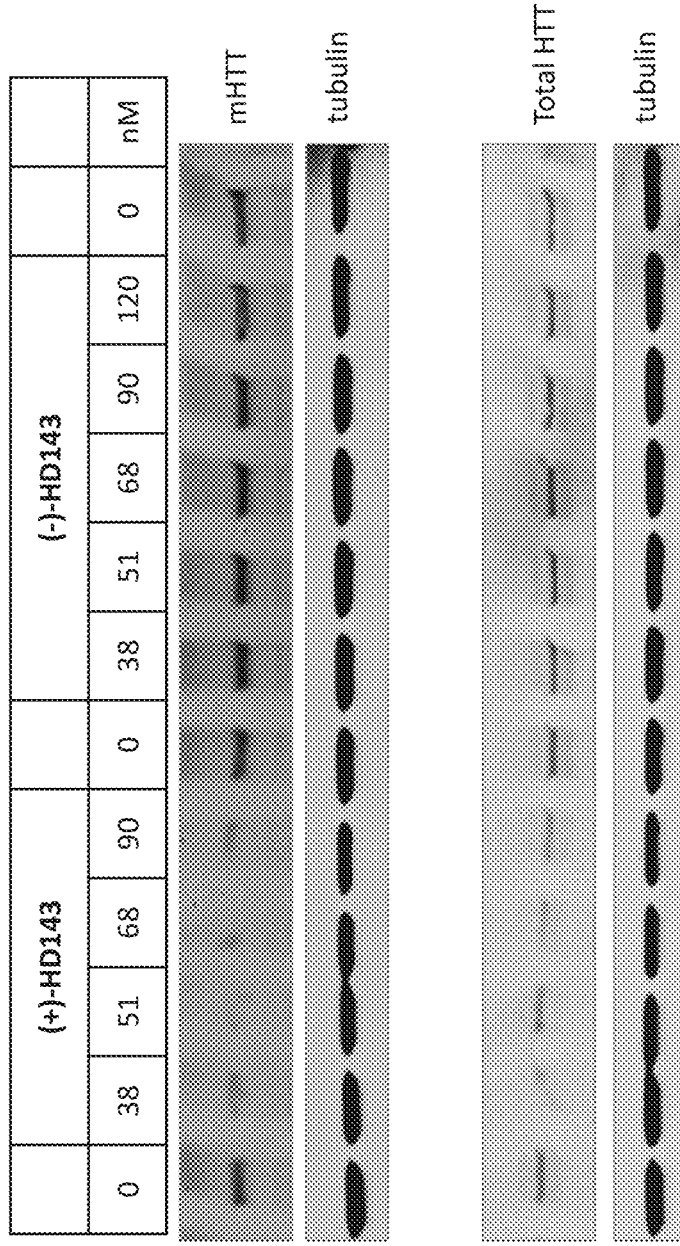
FIG. 3 illustrates the effect of (R)-(+)-HD143 and (S)-(–)-HD143 enantiomers on the mutant HTT protein level in iPSC derived from a Huntington Disease patient. (R)-(+)-HD143 significantly reduced mutant HTT protein level while (S)-(–)-HD143 showed no activity.

The effects of the enantiomeric compounds (+)-HD143 and (−)-HD143 on mutant HTT protein levels in iPSC derived from a Huntington Disease patient were assessed according to the methods described above (see FIG. 3). The results indicate (+)-HD143 significantly reduced mutant HTT protein level while (−)-HD143 showed no activity.

Example 3: Activity of Racemic HD143

1. Biological Properties of Racemic HD143

TABLE 3

| Compound | Luciferase activity (IC50) | Dose to reduce mutant HTT in HD iPSC | IC50 in HD lymphoblastoid cells (mutant Htt reduction) | [Brain]/[Plasma] |
|---|---|---|---|---|
| 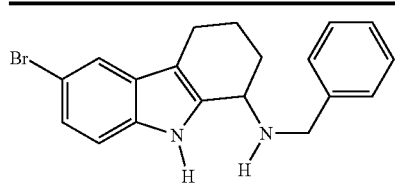 | 30 nm | >=60 nm | 90 nm | 9 at 1 hour following a 5 mg/kg oral dose in rats |

The split *gaussia* luciferase complementation assay measures the interaction between Sup4h and NGN. NGN is the subunit of Supt5h that binds to Supt4h. The data provided above shows that HD143 interrupts the interaction between Sup4h and NGN. The existence of a functional complex of Supt4h and Supt5h has previously been shown to be needed for RNA polymerase I to proceed efficiently though gene regions containing expansions of nucleotide repeats. Interruption of the Supt4h/NGN interaction by HD 143 as demonstrated by the split *gaussia* assay shows that HD143 interrupts the formation of the Supt4h/Supt5h complex. Therefore, administration of HD143 results in decreased production of mutant proteins encoded by genes that include mutant nucleotide repeats.

Using the protocol reported above, iPSCs were treated with HD143 at various doses for 24 hr. The cells were collected and lysed for protein quantification. Equal amounts of protein were applied on SDS-PAGE gel for Western Blotting. Mutant HTT protein was recognized by polyQ antibody (MAB1574 from Millipore) while wild type HTT protein was blotted by anti-Huntingtin antibody (MAB2166 from Millipore). Both proteins were scanned and quantified by Li-Cor Odyssey and normalized by tubulin. HD143 decreases mutant HTT protein in iPSCs derived from a Huntington's disease patient.

Example 4: (+)-HD143 Alleviates Neuron Degeneration Phenotypes of Mutant Htt in *Drosophila* HD Models A. Materials and Methods
1. Fly Stocks The *Drosophila melanogaster* (fruit fly) HD models used in this set of experiments carry the coding sequence of human Httexon1 with 97 CAG repeats to mimic mutant Httof Huntington's disease (HD). The Gmr::Htt97Q fly, expressing mutant Htt primarily in the neurons of *Drosophila* compound eyes, has a severe degeneration of photoreceptor neurons and the phenotypic trait 'rough eye'. All of the fly stocks and genetics crosses were maintained at 25° C. on standard cornmeal yeast agar media.

2. Eye Morphology (Rough Eye) Analysis 15 adult male flies (Gmr-Htt97Q/Gmr-Htt97Q or Gmr/Gmr) were crossed with 15 virgin female flies W1118(+/+) in a vial containing standard yeast agar media with testing compound (+)-HD143 in a concentration of 10 µM or 100 µM. Parent-flies were first removed from vials at day 7, followed by a collection of newly hatched flies for 'rough eye' analysis. The morphology of compound eyes was captured using a Leica DMR upright microscope equipped with a digital camera (CooISNAP 5.0, Photometrics). To increase the depth of field, imaging software was used to create montage composite images (Helicon Focus, HeliconSoft). A total of 10 flies were collected for analysis in each individual condition..

3. Results

Figures 4A, 4B:
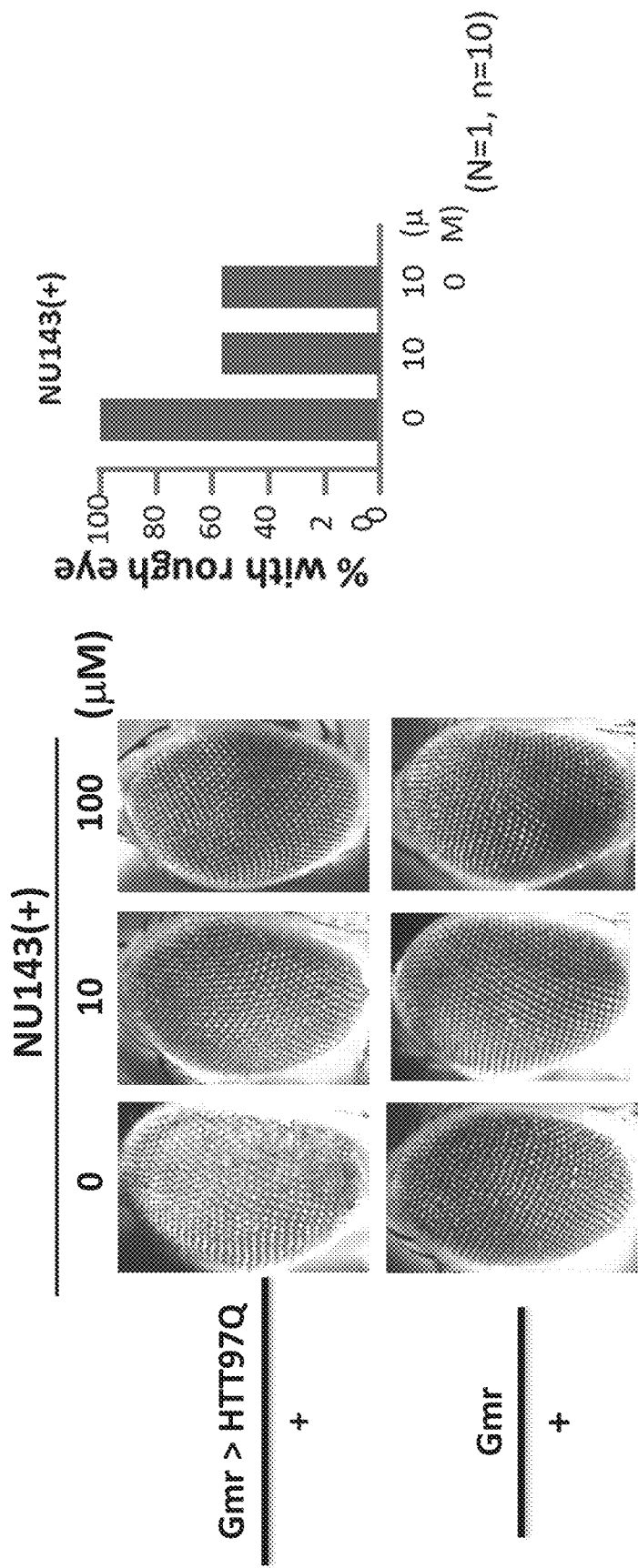
FIG. 4A to FIG. 4B illustrate that (R)-(+)-HD143 alleviates neuron degeneration phenotypes of mutant Htt in *Drosophila* HD models, as reported in the Experimental Section, below.

FIG. 4A. The morphology of compound eye was analyzed in fruit flies treated with or without (+)-HD143. Gmr-Htt97Q/+, a HD fly model showed "rough eye" phenotype, while Gmr/+ was included as a normal control. To quantify the appearance of "rough eye" in Gmr-Htt97Q/+ treated with 10 and 100 µM of (+)-HD143, ten flies were randomly picked from each group and the number of flies with "rough eye" phenotype were determined under microscope. FIG. 4B: Compared to untreated group, the relative percentage of HD flies with "rough eye" phenotype in treated groups is shown (see graph).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A compound, having the structure:

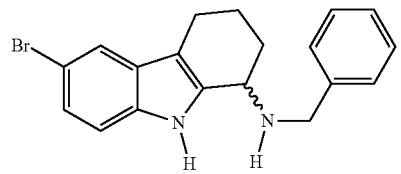 [SMILES: Brc1ccc2[nH]c3c(c2c1)CCCC3NCc1ccccc1]

that is enantiomerically enriched in a (R)-(+)-enantiomer, or a pharmaceutically acceptable salt thereof.

2. The compound according to claim 1, wherein the compound is enantiomerically pure (R)-(+)-N-benzyl-6-bromo-2,3,4,9-tetrahydro-1H-carbazol-1-amine having the structure:

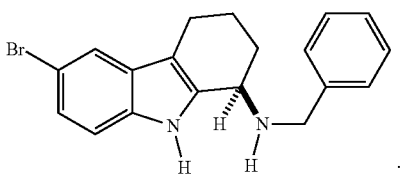 [SMILES: Brc1ccc2[nH]c3c(c2c1)CCC[C@H]3NCc1ccccc1]

3. A pharmaceutical composition comprising:
   a compound according to claim 1, or a pharmaceutically acceptable salt thereof; and
   a pharmaceutically acceptable excipient.

4. A method of treating a subject for a disease or condition associated with the deleterious impact of a mutant extended nucleotide repeat containing target gene, the method comprising:
   administering to a subject in need thereof an effective amount of a compound that is enantiomerically enriched (R)-(+)-N-benzyl-6-bromo-2,3,4,9-tetrahydro-1H-carbazol-1-amine or a pharmaceutically acceptable salt thereof;
   to treat the subject for a disease or condition associated with the deleterious impact of a mutant extended nucleotide repeat containing target gene.

5. The method according to claim 4, wherein the compound is enantiomerically pure (R)-(+)-N-benzyl-6-bromo-2,3,4,9-tetrahydro-1H-carbazol-1-amine having the structure:

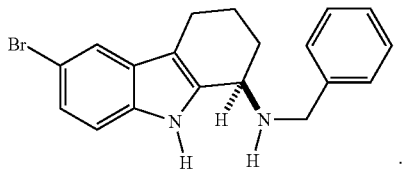

6. The method according to claim 4, wherein the disease or condition is a neurodegenerative disease.

7. The method according to claim 6, wherein the disease or condition is Huntington's disease.

8. The method according to claim 6, wherein the disease or condition is selected from Spinocerebellar ataxia, Dentatorubral pallidoluysian atrophy, amyotrophic lateral sclerosis (ALS) and Spinal and bular muscular atrophy.

9. A method of reducing the deleterious impact of a target gene in a cell, the method comprising:
   contacting a cell with an effective amount of an enantiomerically enriched compound that is (R)-(+)-N-benzyl-6-bromo-2,3,4,9-tetrahydro-1H-carbazol-1-amine or a salt thereof;
   to reduce the deleterious impact in the cell of a target gene comprising a mutant extended nucleotide repeat (NR) domain.

10. The method according to claim 9, wherein the enantiomerically enriched compound is enantiomerically pure (R)-(+)-N-benzyl-6-bromo-2,3,4,9-tetrahydro-1H-carbazol-1-amine.

11. The method according to claim 9, wherein compound reduces expression of a toxic expression product of the target gene.

12. The method according to claim 11, wherein the toxic expression product is a ribonucleic acid expression product.

13. The method according to claim 11, wherein the toxic expression product is a mutant protein.

14. The method according to claim 9, wherein the mutant extended NR domain is a mutant trinucleotide repeat (TNR) domain.

15. The method according to claim 9, wherein the target gene is selected from the group consisting of: ataxin 1, ataxin 2, ataxin 3, ataxin 7, TBP, atrophin 1, androgen receptor protein and huntingtin protein (HTT) genes.

16. The method according to claim 15, wherein the gene is an HTT gene.

17. The method according to claim 9, wherein the compound modulates a function of a SPT4 protein in the cell.

18. A kit, comprising:
   a dose of a compound that is (R)-(+)-N-benzyl-6-bromo-2,3,4,9-tetrahydro-1H-carbazol-1-amine or a pharmaceutically acceptable salt thereof; in an amount effective to treat a subject for a disease or condition associated with the deleterious impact of a mutant extended nucleotide repeat containing target gene; and
   a dose of a second active agent in an amount effective to treat a subject for a disease or condition associated with the deleterious impact of a mutant extended nucleotide repeat containing target gene.

19. The kit of claim 18, wherein the second active agent is selected from an antisense oligonucleotide agent directed to a target gene, nucleoside agent, dopamine-depleting agent; dopamine-receptor antagonists, amantadine, levetiracetam, anticonvulsants, antipsychotic drugs, antiseizure drugs, benzodiazepines, antianxiety, antidepressants, laquinimod, pridopidine, rasagiline, pan-PPAR agonist and RNA silencing agents targeting a HTT single nucleotide polymorphism (SNP).

20. The kit of claim 19, wherein the second active agent is a Huntington's disease agent.

* * * * *